(12) United States Patent
Hastings et al.

(10) Patent No.: US 8,644,934 B2
(45) Date of Patent: Feb. 4, 2014

(54) CARDIAC STIMULATION USING LEADLESS ELECTRODE ASSEMBLIES

(75) Inventors: Roger N. Hastings, Maple Grove, MN (US); Daniel M. Lafontaine, Plymouth, MN (US); Michael J. Pikus, Golden Valley, MN (US); Martin R. Willard, Burnsville, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 1877 days.

(21) Appl. No.: 11/854,844

(22) Filed: Sep. 13, 2007

(65) Prior Publication Data
US 2009/0018599 A1    Jan. 15, 2009

Related U.S. Application Data

(60) Provisional application No. 60/844,599, filed on Sep. 13, 2006.

(51) Int. Cl.
*A61N 1/362* (2006.01)
(52) U.S. Cl.
USPC .............................................. 607/32
(58) Field of Classification Search
USPC ................... 607/60, 32, 65; 128/903
See application file for complete search history.

(56) References Cited

U.S. PATENT DOCUMENTS

| 3,057,356 A | 10/1962 | Greatbatch |
|---|---|---|
| 3,357,434 A | 12/1967 | Abell |
| 3,596,662 A | 8/1971 | Bolduc |
| 3,667,477 A | 6/1972 | Susset et al. |
| 3,713,449 A | 1/1973 | Mulier |
| 3,727,616 A | 4/1973 | Lenzkes |
| 3,835,864 A | 9/1974 | Rasor et al. |
| 3,902,501 A | 9/1975 | Citron et al. |

(Continued)

FOREIGN PATENT DOCUMENTS

| EP | 1166820 A2 | 1/2002 |
|---|---|---|
| EP | 1166832 A1 | 1/2002 |

(Continued)

OTHER PUBLICATIONS

"U.S. Appl. No. 10/971,550, Notice of Allowance mailed Jul. 14, 2008", 4 pgs.

(Continued)

*Primary Examiner* — Christopher D Koharski
*Assistant Examiner* — Jeremiah Kimball
(74) *Attorney, Agent, or Firm* — Schwegman Lundberg & Woessner, P.A.

(57) ABSTRACT

An implantable cardiac tissue excitation system includes an implantable pacing controller unit with a pulse generation circuit. The system also includes a lead with a lead body extending between a proximal lead end attachable to the pacing controller unit and a distal lead end configured to be implanted within a heart. A lead conductor extends within the lead body. The system also includes a transmitter assembly located near the distal lead end that is electrically connected to the pulse generation circuit through the lead conductor to wirelessly transmit pacing control information and pacing energy. The system also includes a leadless electrode assembly configured to be implanted within the heart that includes a receiver to receive the wireless transmission, a charge storage unit to store the charge energy, and an electrical stimulation circuit to deliver an electrical stimulus to cardiac tissue using the pacing control information and the charge energy.

37 Claims, 16 Drawing Sheets

(56) References Cited

U.S. PATENT DOCUMENTS

| | | | |
|---|---|---|---|
| 3,942,535 A | 3/1976 | Schulman | |
| 3,943,936 A | 3/1976 | Rasor et al. | |
| 4,157,720 A | 6/1979 | Greatbatch | |
| 4,162,679 A | 7/1979 | Reenstierna | |
| 4,198,991 A | 4/1980 | Harris | |
| 4,256,115 A | 3/1981 | Bilitch | |
| 4,441,210 A | 4/1984 | Hochmair et al. | |
| 4,543,955 A * | 10/1985 | Schroeppel | 600/348 |
| 4,641,664 A | 2/1987 | Botvidsson | |
| 4,644,957 A | 2/1987 | Ricciardelli | |
| 4,681,111 A | 7/1987 | Silvian | |
| 4,721,118 A | 1/1988 | Harris | |
| 4,830,006 A | 5/1989 | Haluska et al. | |
| 4,858,623 A | 8/1989 | Bradshaw et al. | |
| 4,860,750 A | 8/1989 | Frey et al. | |
| 4,953,564 A | 9/1990 | Berthelsen | |
| 4,987,897 A * | 1/1991 | Funke | 607/32 |
| 5,113,869 A * | 5/1992 | Nappholz et al. | 600/508 |
| 5,139,033 A | 8/1992 | Everett et al. | |
| 5,143,090 A | 9/1992 | Dutcher et al. | |
| 5,170,802 A | 12/1992 | Mehra | |
| 5,178,149 A | 1/1993 | Imburgia et al. | |
| 5,193,539 A | 3/1993 | Schulman et al. | |
| 5,193,540 A | 3/1993 | Schulman et al. | |
| 5,234,437 A | 8/1993 | Sepetka | |
| 5,243,977 A | 9/1993 | Trabucco et al. | |
| 5,246,014 A | 9/1993 | Williams et al. | |
| 5,250,071 A | 10/1993 | Palermo | |
| 5,255,693 A | 10/1993 | Dutcher et al. | |
| 5,261,916 A | 11/1993 | Engelson | |
| 5,300,107 A | 4/1994 | Stokes et al. | |
| 5,304,195 A | 4/1994 | Twyford, Jr. et al. | |
| 5,312,415 A | 5/1994 | Palermo | |
| 5,312,439 A | 5/1994 | Loeb | |
| 5,314,458 A | 5/1994 | Najafi et al. | |
| 5,324,316 A | 6/1994 | Schulman et al. | |
| 5,324,325 A | 6/1994 | Moaddeb | |
| 5,335,664 A | 8/1994 | Nagashima | |
| 5,350,397 A | 9/1994 | Palermo et al. | |
| 5,383,924 A | 1/1995 | Brehier | |
| 5,405,367 A | 4/1995 | Schulman et al. | |
| 5,411,535 A | 5/1995 | Fujii et al. | |
| 5,411,537 A | 5/1995 | Munshi et al. | |
| 5,447,533 A | 9/1995 | Vachon et al. | |
| 5,487,760 A | 1/1996 | Villafana | |
| 5,531,780 A | 7/1996 | Vachon | |
| 5,571,148 A | 11/1996 | Loeb et al. | |
| 5,591,217 A | 1/1997 | Barreras | |
| 5,622,168 A | 4/1997 | Keusch et al. | |
| 5,628,778 A | 5/1997 | Kruse et al. | |
| 5,674,259 A | 10/1997 | Gray | |
| 5,735,887 A | 4/1998 | Barreras, Sr. et al. | |
| 5,755,764 A | 5/1998 | Schroeppel | |
| 5,769,877 A | 6/1998 | Barreras, Sr. | |
| 5,779,715 A | 7/1998 | Tu | |
| 5,792,208 A | 8/1998 | Gray | |
| 5,800,535 A | 9/1998 | Howard, III | |
| 5,807,397 A | 9/1998 | Barreras | |
| 5,814,089 A | 9/1998 | Stokes et al. | |
| 5,833,715 A | 11/1998 | Vachon et al. | |
| 5,851,227 A | 12/1998 | Spehr | |
| 5,861,019 A * | 1/1999 | Sun et al. | 607/60 |
| 5,871,532 A | 2/1999 | Schroeppel | |
| 5,876,431 A | 3/1999 | Spehr et al. | |
| 5,954,757 A | 9/1999 | Gray | |
| 5,995,876 A | 11/1999 | Kruse et al. | |
| 6,006,139 A | 12/1999 | Kruse et al. | |
| 6,035,239 A | 3/2000 | Patag et al. | |
| 6,041,258 A | 3/2000 | Cigaina et al. | |
| 6,044,300 A | 3/2000 | Gray | |
| 6,123,724 A | 9/2000 | Denker | |
| 6,132,456 A | 10/2000 | Sommer et al. | |
| 6,141,588 A | 10/2000 | Cox et al. | |
| 6,144,879 A | 11/2000 | Gray | |
| 6,144,880 A | 11/2000 | Ding et al. | |
| 6,161,029 A | 12/2000 | Spreigl et al. | |
| 6,164,284 A | 12/2000 | Schulman et al. | |
| 6,200,303 B1 | 3/2001 | Verrior et al. | |
| 6,208,894 B1 | 3/2001 | Schulman et al. | |
| 6,223,079 B1 | 4/2001 | Bakels et al. | |
| 6,240,316 B1 | 5/2001 | Richmond et al. | |
| 6,266,567 B1 | 7/2001 | Ishikawa et al. | |
| 6,315,721 B2 | 11/2001 | Schulman et al. | |
| 6,336,937 B1 | 1/2002 | Vonesh et al. | |
| 6,345,202 B2 | 2/2002 | Richmond et al. | |
| 6,351,673 B1 | 2/2002 | Ding et al. | |
| 6,360,127 B1 | 3/2002 | Ding et al. | |
| 6,363,279 B1 | 3/2002 | Ben-Haim et al. | |
| 6,363,938 B2 | 4/2002 | Saadat et al. | |
| 6,370,434 B1 | 4/2002 | Zhang et al. | |
| 6,381,495 B1 | 4/2002 | Jenkins | |
| 6,385,472 B1 | 5/2002 | Hall et al. | |
| 6,409,674 B1 | 6/2002 | Brockway et al. | |
| 6,441,747 B1 | 8/2002 | Khair et al. | |
| 6,445,953 B1 | 9/2002 | Bulkes et al. | |
| 6,456,256 B1 | 9/2002 | Amundson et al. | |
| 6,501,983 B1 | 12/2002 | Natarajan et al. | |
| 6,542,775 B2 | 4/2003 | Ding et al. | |
| 6,556,874 B2 | 4/2003 | Audoglio | |
| 6,564,807 B1 | 5/2003 | Schulman et al. | |
| 6,582,441 B1 | 6/2003 | He et al. | |
| 6,589,230 B2 | 7/2003 | Gia et al. | |
| 6,647,291 B1 | 11/2003 | Bonner et al. | |
| 6,647,292 B1 | 11/2003 | Bardy et al. | |
| 6,783,499 B2 | 8/2004 | Schwartz | |
| 6,856,836 B2 | 2/2005 | Ding et al. | |
| 6,859,665 B2 | 2/2005 | Ding et al. | |
| 6,895,265 B2 | 5/2005 | Silver | |
| 6,895,280 B2 | 5/2005 | Meadows et al. | |
| 6,897,788 B2 | 5/2005 | Khair et al. | |
| 6,907,285 B2 | 6/2005 | Denker et al. | |
| 6,917,833 B2 | 7/2005 | Denker et al. | |
| 7,003,350 B2 | 2/2006 | Denker et al. | |
| 7,006,864 B2 | 2/2006 | Echt et al. | |
| 7,050,849 B2 | 5/2006 | Echt et al. | |
| 7,054,691 B1 * | 5/2006 | Kuzma et al. | 607/57 |
| 7,062,318 B2 | 6/2006 | Ben-Haim et al. | |
| 7,076,305 B2 | 7/2006 | Imran et al. | |
| 7,184,830 B2 | 2/2007 | Echt et al. | |
| 7,200,437 B1 | 4/2007 | Nabutovsky et al. | |
| 7,209,783 B2 | 4/2007 | Fellows et al. | |
| 7,231,260 B2 | 6/2007 | Wallace et al. | |
| 7,289,853 B1 | 10/2007 | Campbell et al. | |
| 7,410,497 B2 | 8/2008 | Hastings et al. | |
| 7,522,962 B1 | 4/2009 | Doron et al. | |
| 7,532,932 B2 | 5/2009 | Denker et al. | |
| 7,532,933 B2 | 5/2009 | Hastings et al. | |
| 7,558,631 B2 | 7/2009 | Cowan et al. | |
| 7,565,195 B1 | 7/2009 | Kroll et al. | |
| 7,606,621 B2 | 10/2009 | Brisken et al. | |
| 7,610,092 B2 | 10/2009 | Cowan et al. | |
| 7,615,010 B1 | 11/2009 | Najafi et al. | |
| 7,634,313 B1 | 12/2009 | Kroll et al. | |
| 7,647,109 B2 | 1/2010 | Hastings et al. | |
| 7,650,186 B2 | 1/2010 | Hastings et al. | |
| 7,702,392 B2 | 4/2010 | Echt et al. | |
| 7,765,001 B2 | 7/2010 | Echt et al. | |
| 7,809,438 B2 | 10/2010 | Echt et al. | |
| 7,840,281 B2 | 11/2010 | Kveen et al. | |
| 7,848,815 B2 | 12/2010 | Brisken et al. | |
| 7,848,823 B2 | 12/2010 | Drasler et al. | |
| 7,877,136 B2 | 1/2011 | Moffitt et al. | |
| 7,877,142 B2 | 1/2011 | Moaddeb et al. | |
| 7,890,173 B2 | 2/2011 | Brisken et al. | |
| 7,894,904 B2 | 2/2011 | Cowan et al. | |
| 7,894,907 B2 | 2/2011 | Cowan et al. | |
| 7,894,910 B2 | 2/2011 | Cowan et al. | |
| 7,899,537 B1 | 3/2011 | Kroll et al. | |
| 7,899,541 B2 | 3/2011 | Cowan et al. | |
| 7,899,542 B2 | 3/2011 | Cowan et al. | |
| 7,904,170 B2 | 3/2011 | Harding | |
| 7,937,148 B2 | 5/2011 | Jacobson | |
| 7,937,161 B2 | 5/2011 | Hastings et al. | |
| 7,945,333 B2 | 5/2011 | Jacobson | |

(56) References Cited

U.S. PATENT DOCUMENTS

| | | |
|---|---|---|
| 7,996,087 B2 | 8/2011 | Cowan et al. |
| 8,010,209 B2 | 8/2011 | Jacobson |
| 8,019,419 B1 | 9/2011 | Panescu et al. |
| 8,032,219 B2 | 10/2011 | Neumann et al. |
| 8,050,774 B2 | 11/2011 | Kveen et al. |
| 8,165,694 B2 | 4/2012 | Carbanaru et al. |
| 8,185,213 B2 | 5/2012 | Kveen et al. |
| 8,204,595 B2 | 6/2012 | Pianca et al. |
| 8,204,605 B2 | 6/2012 | Hastings et al. |
| 8,260,416 B2 | 9/2012 | Ben-Haim et al. |
| 8,290,600 B2 | 10/2012 | Hastings et al. |
| 8,332,036 B2 | 12/2012 | Hastings et al. |
| 8,340,780 B2 | 12/2012 | Hastings et al. |
| 2001/0018547 A1 | 8/2001 | Mechlenburg et al. |
| 2002/0026228 A1 | 2/2002 | Schauerte |
| 2002/0052632 A1 | 5/2002 | Ben-Haim et al. |
| 2002/0065543 A1 | 5/2002 | Gomperz et al. |
| 2002/0077556 A1 | 6/2002 | Schwartz |
| 2002/0077685 A1 | 6/2002 | Sundquist et al. |
| 2002/0123774 A1 | 9/2002 | Loeb et al. |
| 2002/0123785 A1 | 9/2002 | Zhang et al. |
| 2002/0138009 A1 | 9/2002 | Brockway et al. |
| 2002/0183791 A1 | 12/2002 | Denker et al. |
| 2002/0198604 A1 | 12/2002 | Schulman et al. |
| 2003/0036773 A1 | 2/2003 | Whitehurst et al. |
| 2003/0050681 A1 | 3/2003 | Pianca et al. |
| 2003/0088278 A1 | 5/2003 | Bardy |
| 2003/0109914 A1 | 6/2003 | Westlund et al. |
| 2003/0181958 A1 | 9/2003 | Dobak |
| 2003/0181959 A1 | 9/2003 | Dobak |
| 2004/0059392 A1 | 3/2004 | Parramon et al. |
| 2004/0098068 A1 | 5/2004 | Carbunaru et al. |
| 2004/0102830 A1 | 5/2004 | Williams |
| 2004/0103906 A1 | 6/2004 | Schulman et al. |
| 2004/0106954 A1 | 6/2004 | Whitehurst et al. |
| 2004/0147973 A1 | 7/2004 | Hauser et al. |
| 2004/0171355 A1 | 9/2004 | Yu et al. |
| 2004/0215280 A1* | 10/2004 | Dublin et al. ............ 607/36 |
| 2004/0254419 A1 | 12/2004 | Wang et al. |
| 2005/0021108 A1 | 1/2005 | Klosterman et al. |
| 2005/0057905 A1 | 3/2005 | He et al. |
| 2005/0060011 A1 | 3/2005 | Denker et al. |
| 2005/0096702 A1 | 5/2005 | Denker et al. |
| 2005/0131511 A1 | 6/2005 | Westlund |
| 2005/0149138 A1 | 7/2005 | Min et al. |
| 2005/0182456 A1 | 8/2005 | Ziobro et al. |
| 2005/0182465 A1 | 8/2005 | Ness |
| 2005/0251238 A1 | 11/2005 | Wallace et al. |
| 2005/0251240 A1 | 11/2005 | Doan |
| 2005/0261741 A1 | 11/2005 | Libbus et al. |
| 2005/0288717 A1 | 12/2005 | Sunagawa |
| 2005/0288727 A1 | 12/2005 | Penner |
| 2006/0015097 A1 | 1/2006 | Mulier et al. |
| 2006/0020316 A1 | 1/2006 | Martinez et al. |
| 2006/0064135 A1 | 3/2006 | Brockway |
| 2006/0085039 A1* | 4/2006 | Hastings et al. ............ 607/9 |
| 2006/0085041 A1 | 4/2006 | Hastings et al. |
| 2006/0085042 A1 | 4/2006 | Hastings et al. |
| 2006/0136001 A1 | 6/2006 | Ortega et al. |
| 2006/0136004 A1 | 6/2006 | Cowan et al. |
| 2006/0173504 A1 | 8/2006 | Zhu et al. |
| 2006/0173505 A1 | 8/2006 | Salo et al. |
| 2006/0178719 A1 | 8/2006 | Ideker et al. |
| 2006/0206170 A1 | 9/2006 | Denker et al. |
| 2006/0241705 A1 | 10/2006 | Neumann et al. |
| 2007/0075905 A1 | 4/2007 | Denker et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0106357 A1 | 5/2007 | Denker et al. |
| 2007/0135882 A1 | 6/2007 | Drasler et al. |
| 2007/0135883 A1 | 6/2007 | Drasler et al. |
| 2007/0150009 A1 | 6/2007 | Kveen et al. |
| 2007/0150037 A1 | 6/2007 | Hastings et al. |
| 2007/0150038 A1 | 6/2007 | Hastings et al. |
| 2007/0162079 A1 | 7/2007 | Shemer et al. |
| 2007/0203556 A1 | 8/2007 | Rutten et al. |
| 2007/0219590 A1 | 9/2007 | Hastings et al. |
| 2007/0239248 A1 | 10/2007 | Hastings et al. |
| 2007/0276444 A1 | 11/2007 | Gelbart et al. |
| 2007/0293904 A1 | 12/2007 | Gelbart et al. |
| 2008/0021505 A1 | 1/2008 | Hastings et al. |
| 2008/0021532 A1 | 1/2008 | Kveen et al. |
| 2008/0039904 A1 | 2/2008 | Bulkes et al. |
| 2008/0046040 A1 | 2/2008 | Denker et al. |
| 2008/0077184 A1 | 3/2008 | Denker et al. |
| 2008/0077188 A1 | 3/2008 | Denker et al. |
| 2008/0109054 A1 | 5/2008 | Hastings et al. |
| 2008/0140142 A1 | 6/2008 | Darvish et al. |
| 2008/0262588 A1 | 10/2008 | Zarembo et al. |
| 2008/0288039 A1 | 11/2008 | Reddy |
| 2008/0306359 A1* | 12/2008 | Zdeblick et al. ............ 600/302 |
| 2008/0319502 A1 | 12/2008 | Sunagawa et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0204170 A1 | 8/2009 | Hastings et al. |
| 2009/0234407 A1 | 9/2009 | Hastings et al. |
| 2009/0275998 A1 | 11/2009 | Burnes et al. |
| 2010/0094367 A1 | 4/2010 | Sen |
| 2010/0100144 A1 | 4/2010 | Shuros et al. |
| 2010/0198288 A1 | 8/2010 | Ostroff |
| 2010/0228308 A1 | 9/2010 | Cowan et al. |
| 2010/0286744 A1 | 11/2010 | Echt et al. |
| 2011/0034939 A1 | 2/2011 | Kveen et al. |
| 2011/0071586 A1 | 3/2011 | Jacobson |
| 2011/0077708 A1 | 3/2011 | Ostroff |
| 2011/0190835 A1 | 8/2011 | Brockway et al. |
| 2011/0208260 A1 | 8/2011 | Jacobson |
| 2011/0213233 A1 | 9/2011 | Stevenson et al. |
| 2011/0218587 A1 | 9/2011 | Jacobson |
| 2011/0237967 A1 | 9/2011 | Moore et al. |
| 2011/0251660 A1 | 10/2011 | Griswold |
| 2011/0251662 A1 | 10/2011 | Griswold et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2012/0078322 A1 | 3/2012 | Dal Molin et al. |
| 2012/0089198 A1 | 4/2012 | Ostroff |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0158111 A1 | 6/2012 | Khairkhahan et al. |
| 2012/0172690 A1 | 7/2012 | Anderson et al. |
| 2012/0232565 A1 | 9/2012 | Kveen et al. |

FOREIGN PATENT DOCUMENTS

| | | |
|---|---|---|
| EP | 1264572 A1 | 12/2002 |
| EP | 1809372 A1 | 7/2007 |
| EP | 1812104 A1 | 8/2007 |
| EP | 1835962 A1 | 9/2007 |
| JP | 61-203730 A | 9/1986 |
| JP | 62-254770 A | 6/1987 |
| JP | 2-307481 A | 12/1990 |
| JP | 05076501 A2 | 3/1993 |
| JP | 05-245215 A | 9/1993 |
| JP | 05245215 A | 9/1993 |
| JP | 6-510459 A | 11/1994 |
| JP | 7-016299 A | 1/1995 |
| JP | 9-508054 A | 8/1997 |
| JP | 10-509901 A | 9/1998 |
| JP | 2000-502931 A | 3/2000 |
| JP | 2001-511406 A | 8/2001 |
| JP | 2002-510222 A | 4/2002 |
| JP | 2002-514478 A | 5/2002 |
| JP | 2004-173790 A | 6/2004 |
| JP | 5153892 B2 | 2/2013 |
| NZ | 526115 | 10/2006 |

(56) References Cited

FOREIGN PATENT DOCUMENTS

| NZ | 539770 | 10/2007 |
|---|---|---|
| NZ | 539771 | 10/2007 |
| WO | WO-93/08871 A1 | 5/1993 |
| WO | WO-95/10226 A1 | 4/1995 |
| WO | WO-96/20754 A1 | 7/1996 |
| WO | WO-97/25098 A1 | 7/1997 |
| WO | WO-98/26840 A1 | 6/1998 |
| WO | WO-99/06102 A1 | 2/1999 |
| WO | WO-99/58191 A1 | 11/1999 |
| WO | WO-99/64104 A1 | 12/1999 |
| WO | WO-00/30534 A1 | 6/2000 |
| WO | WO-01/00114 A1 | 1/2001 |
| WO | WO-03/041793 A2 | 5/2003 |
| WO | WO-03/053491 A2 | 7/2003 |
| WO | WO-03/076010 A1 | 9/2003 |
| WO | WO-2004/002572 A1 | 1/2004 |
| WO | WO-2004/012811 A1 | 2/2004 |
| WO | WO-2006/045073 A1 | 4/2006 |
| WO | WO-2006/045074 A2 | 4/2006 |
| WO | WO-2006/045075 A1 | 4/2006 |
| WO | WO-2006/096685 A1 | 9/2006 |
| WO | WO-2007/067253 A1 | 6/2007 |
| WO | WO-2007/078770 A2 | 7/2007 |
| WO | WO-2007/112004 A2 | 10/2007 |
| WO | WO-2007/115044 A2 | 10/2007 |
| WO | WO-2008/034005 A2 | 3/2008 |
| WO | WO-2009/099550 A1 | 8/2009 |
| WO | WO-2009/099597 A1 | 8/2009 |
| WO | WO-2012082755 A1 | 6/2012 |

OTHER PUBLICATIONS

"U.S. Appl. No. 10/971,550, Response filed Feb. 22, 2007 to Restriction Requirement mailed Jan. 22, 2007", 1 pg.

"U.S. Appl. No. 10/971,550, Restriction Requirement mailed Jan. 22, 2007", 22 pgs.

"U.S. Appl. No. 10/971,550, Notice of Allowance mailed Dec. 22, 2008", 4 pgs.

"U.S. Appl. No. 10/971,550, Non-Final Office Action mailed Mar. 19, 2007", 11 pgs.

"U.S. Appl. No. 10/971,550, Non-Final Office Action mailed Nov. 5, 2007", 19 pgs.

"U.S. Appl. No. 10/971,550, Amendment filed Sep. 4, 2007 to Non-Final Office Action mailed Mar. 19, 2007", 15 pgs.

"U.S. Appl. No. 10/971,550, Response filed Mar. 25, 2008 to Non-Final Office Action mailed Nov. 5, 2007", 17 pgs.

"U.S. Appl. No. 10/971,550, Amendment Under 37 C.F.R. Sec. 1.312 filed Mar. 20, 2009", 6 pgs.

"U.S. Appl. No. 11/075,375, Response filed May 7, 2007 to Restriction Requirement mailed Apr. 10, 2007", 8 pgs.

"U.S. Appl. No. 11/075,375, Restriction Requirement mailed Apr. 10, 2007", 6 pgs.

"U.S. Appl. No. 11/075,375, Response filed May 22, 2008 to Final Office Action mailed Jan. 23, 2008", 16 pgs.

"U.S. Appl. No. 11/075,375, Non-Final Office Action mailed Jun. 8, 2007", 11 pgs.

"U.S. Appl. No. 11/075,375, Amendment filed Oct. 26, 2007 to Non-Final Office Action mailed Jun. 8, 2007", 10 pgs.

"U.S. Appl. No. 11/075,375, Final Office Action mailed Jan. 23, 2008", 10 pgs.

"U.S. Appl. No. 11/075,375, Amendment and Response filed Jan. 12, 2009 to Non-Final Office Action mailed Aug. 11, 2009", 18 pgs.

"U.S. Appl. No. 11/075,375, Non-Final Office Action mailed Aug. 11, 2008", 15 pgs.

"U.S. Appl. No. 11/075,375, Final Office Action mailed Apr. 16, 2009", 10 pgs.

"U.S. Appl. No. 11/075,375, Response filed Jul. 16, 2009 to Final Office Actin mailed Apr. 16, 2009", 13 pgs.

"U.S. Appl. No. 11/075,376, Response filed Jun. 9, 2008 to Final Office Action mailed Jan. 7, 2008", 20 pgs.

"U.S. Appl. No. 11/075,376, Non-Final Office Action Mailed Aug. 20, 2008", 15 pgs.

"U.S. Appl. No. 11/075,376, Response and Preliminary Amendment filed May 7, 2007 to Restriction Requirement mailed Apr. 10, 2007", 8 pgs.

"U.S. Appl. No. 11/075,376, Final Office Action mailed Jan. 7, 2008", 11 pgs.

"U.S. Appl. No. 11/075,376, Non-Final Office Action mailed Jun. 26, 2007", 9 pgs.

"U.S. Appl. No. 11/075,376, Response filed Jan. 21, 2009 to Non-Final Office Action mailed Aug. 20, 2008", 22 pgs.

"U.S. Appl. No. 11/075,376, Amendment filed Oct. 26, 2007 to Non-Final Office Action mailed Jun. 26, 2007", 14 pgs.

"U.S. Appl. No. 11/075,376, Restriction Requirement mailed Apr. 10, 2007", 6 pgs.

"U.S. Appl. No. 11/075,376, Final Office Action mailed Apr. 8, 2009", 17 pgs.

"U.S. Appl. No. 11/075,376, Notice of Allowance mailed Aug. 24, 2009", 6 pgs.

"U.S. Appl. No. 11/075,376, Response filed Jul. 8, 2009 to Final Office Action mailed Apr. 8, 2009", 11 pgs.

"U.S. Appl. No. 11/394,601, Non-Final Office Action mailed Sep. 2, 2009", 6 pgs.

"U.S. Appl. No. 11/394,601, Response filed May 4, 2009 to Restriction Requirement mailed Apr. 2, 2009", 9 pgs.

"U.S. Appl. No. 11/394,601, Restriction Requirement mailed Apr. 2, 2009", 10 pgs.

"U.S. Appl. No. 11/549,352, Non-Final Office Action mailed Feb. 5, 2008", 11 pgs.

"U.S. Appl. No. 11/549,352, Final Office Action mailed Mar. 9, 2009", 10 pgs.

"U.S. Appl. No. 11/549,352, Notice of Panel Decision from Pre-Appeal Brief Review mailed Feb. 2, 2009", 2 pgs.

"U.S. Appl. No. 11/549,352, Pre-Appeal Brief for Review filed Dec. 20, 2008", 5 pgs.

"U.S. Appl. No. 11/549,352, Response filed Jul. 7, 2008 to Non-Final Office Action mailed Feb. 5, 2008", 17 pgs.

"U.S. Appl. No. 11/549,352, Final Office Action mailed Aug. 26, 2008", 13 pgs.

"U.S. Appl. No. 11/549,352, Appeal Brief filed Sep. 9, 2009", 37 pgs.

"U.S. Appl. No. 11/683,577, Final Office Action mailed Nov. 9, 2009", 14 pgs.

"U.S. Appl. No. 11/683,577, Non-Final Office Action mailed Mar. 5, 2009", 13 pgs.

"U.S. Appl. No. 11/683,577, Response filed Aug. 5, 2009 to Non Final Office Action mailed Mar. 5, 2009", 10 pgs.

"U.S. Appl. No. 11/683,584, Non-Final Office Action mailed Apr. 1, 2009", 9 pgs.

"U.S. Appl. No. 11/683,584, Response filed Jul. 1, 2009 to Non Final Office Action mailed Apr. 1, 2009", 7 pgs.

"U.S. Appl. No. 11/745,070, Non Final Office Action mailed Apr. 27, 2009", 11 pgs.

"U.S. Appl. No. 11/745,070, Response filed Jul. 27, 2009 to Non Final Office Action mailed Apr. 27, 2009", 11 pgs.

"U.S. Appl. No. 11/745,105, Non-Final Office Action mailed Sep. 18, 2009", 9 pgs.

"Breakthrough Products Could Put Lesser-Known Firms on the Map", (2004), 56-58.

"European Application Serial No. 07759589.0, Office Action mailed Jan. 29, 2009", 3 pgs.

"European Application Serial No. 07759589.0, Response filed Jun. 5, 2009 to Office Action mailed Jan. 29, 2009", 6 pgs.

"International Application Serial No. PCT/US2006/040291 International Search Report mailed Apr. 4, 2007", 5 pgs.

"International Application Serial No. PCT/US2006/040291 Written Opinion mailed Apr. 4, 2007", 9 pgs.

"International Application Serial No. PCT/US2005/037978, International Search Report mailed Jun. 13, 2006", 5 pgs.

"International Application Serial No. PCT/US2005/037978, Written Opinion mailed Jun. 13, 2006", 12 pgs.

"International Application Serial No. PCT/US2005/037979, International Search Report mailed Mar. 21, 2006", 4 pgs.

(56) References Cited

OTHER PUBLICATIONS

"International Application Serial No. PCT/US2005/037979, Written Opinion mailed Mar. 21, 2006", 8 pgs.

"International Application Serial No. PCT/US2007/078405, International Search Report mailed May 20, 2008", 5 pgs.

"International Application Serial No. PCT/US2007/078405, Written Opinion mailed May 20, 2008", 7 pgs.

"International Application Serial No. PCT/US2009/000693, International Search Report mailed May 8, 2009", 5 pgs.

"International Application Serial No. PCT/US2009/000693, Written Opinion mailed May, 8, 2009", 8 pgs.

"Telemetry Research Transcutaneous Energy Transfer (TET) Technology Summary", *Telemetry Research Ltd.*, www.telemetryresearch.com, (No date listed), 1 pg.

Busch, M., et al., "On the Heating of Inductively Coupled Resonators (Stents) During MRI Examinations", *Magnetic Resonance in Medicine*, 54, (2005), 775-785.

Manoharan, G., et al., "Novel passive implantable atrial defibrillator using transcutaneous radiofrequency energy transmission successfully cardioverts atrial fibrillation.", *Circulation*, 108(11), (Sep. 16, 2003), 1382-1388.

Piella, J. P., "Energy management, wireless and system solutions for highly integrated implantable devices", *Doctoral Thesis. Universitat Autonoma de Barcelona*, (Dec. 2001), 62 pgs.

Si, Ping, et al., "A Frequency Control Method for Regulating Wireless Power to Implantable Devices", *IEEE Transactions on Biomedical Circuits and Systems*, 2(1), (Mar. 2008), 22-29.

Swain, E., "Breakthrough Products Could Put Lesser-Known Firms on the map", *MDDI*,(Apr. 2004), 6 pgs.

Wagner, B. K, "Chapter 6—Electrodes, Leads, and Biocompatibility", *Design of Cardiac Pacemakers*, edited by John G. Webster., (1995), 133-160.

"U.S. Appl. No. 11/394,601, Notice of Allowance mailed Dec. 28, 2010", 8 pgs.

"U.S. Appl. No. 10/971,550, Examiner Interview Summary mailed Jan. 22, 2008", 4 pgs.

"U.S. Appl. No. 11/075,375, Examiner Interview Summary mailed Jan. 12, 2009", 4 pgs.

"U.S. Appl. No. 11/075,375, Examiner Interview Summary mailed May 1, 2008", 4 pgs.

"U.S. Appl. No. 11/075,375, Notice of Allowance mailed Sep. 4, 2009", 6 pgs.

"U.S. Appl. No. 11/075,376, Examiner Interview Summary mailed Jan. 12, 2009", 4 pgs.

"U.S. Appl. No. 11/075,376, Examiner Interview Summary mailed Apr. 2, 2008", 4 pgs.

"U.S. Appl. No. 11/316,120 Final Office Action mailed Oct. 28, 2010", 8 pgs.

"U.S. Appl. No. 11/316,120, Non Final Office Action mailed Apr. 11, 2008", 7 pgs.

"U.S. Appl. No. 11/316,120, Non-Final Office Action mailed May 27, 2010", 7 pgs.

"U.S. Appl. No. 11/316,120, Response filed Apr. 12, 2010 to Final Office Action mailed Nov. 12, 2009", 12 pgs.

"U.S. Appl. No. 11/316,120, Response filed May 14, 2008 to Non Final Office Action mailed Apr. 11, 2008", 12 pgs.

"U.S. Appl. No. 11/316,120, Response filed Aug. 27, 2010 to Non Final Office Action mailed May 27, 2010", 13 Pgs.

"U.S. Appl. No. 11/394,601, Final Office Action mailed Mar. 22, 2010", 7 pgs.

"U.S. Appl. No. 11/394,601, Pre-Appeal Brief Request filed Jul. 21, 2010", 5 pgs.

"U.S. Appl. No. 11/490,576, Final Office Action mailed Jan. 19, 2011", 13 pgs.

"U.S. Appl. No. 11/490,576, Non-Final Office Action mailed Jul. 12, 2010", 9 pgs.

"U.S. Appl. No. 11/490,576, Response filed Mar. 5, 2010 to Non Final Office Action mailed Oct. 5, 2009", 13 pgs.

"U.S. Appl. No. 11/490,576, Response filed Oct. 4, 2010 to Non Final Office Action mailed Jul. 12, 2010", 15 pgs.

"U.S. Appl. No. 11/490,916, Examiner Interview Summary mailed Apr. 12, 2010", 3 pgs.

"U.S. Appl. No. 11/490,916, Examiner Interview Summary mailed Aug. 19, 2009", 2 pgs.

"U.S. Appl. No. 11/490,916, Notice of Allowance mailed Jul. 9, 2010", 4 pgs.

"U.S. Appl. No. 11/490,916, Response filed Jan. 12, 2009 to Restriction Requirement Dec. 11, 2008", 7 pgs.

"U.S. Appl. No. 11/490,916, Response filed Apr. 15, 2010 to Final Office Action mailed Dec. 17, 2009", 12 pgs.

"U.S. Appl. No. 11/490,916, Supplemental Notice of Allowability Mailed Oct. 14, 2010", 2 pgs.

"U.S. Appl. No. 11/511,152, Notice of Allowance mailed Jul. 28, 2010", 6 pgs.

"U.S. Appl. No. 11/511,152, Preliminary Amendment filed Oct. 17, 2006", 3 pgs.

"U.S. Appl. No. 11/511,152, Response filed Jun. 30, 2010 to Non-Final Office Action mailed Dec. 30, 2009", 12 pgs.

"U.S. Appl. No. 11/549,352, Examiner Interview Summary mailed Jun. 25, 2008", 2 pgs.

"U.S. Appl. No. 11/549,352, Examiner's Answer mailed Nov. 27, 2009 to Appeal Brief filed Sep. 9. 2009", 12 pgs.

"U.S. Appl. No. 11/549,352, Reply Brief filed Jan. 27, 2010", 8 pgs.

"U.S. Appl. No. 11/683,577, Examiner Interview Summary mailed Jul. 7, 2009", 4 pgs.

"U.S. Appl. No. 11/683,577, Response filed May 7, 2010 to Final Office Action mailed Nov. 9, 2009", 14 pgs.

"U.S. Appl. No. 11/683,584, Examiner Interview Summary mailed Jul. 7, 2009", 4 pgs.

"U.S. Appl. No. 11/683,584, Final Office Action mailed Jan. 29, 2010", 9 pgs.

"U.S. Appl. No. 11/683,584, Preliminary Amendment filed Mar. 8, 2007", 1 pg.

"U.S. Appl. No. 11/683,584, Response filed Jul. 21, 2010 to Final Office Action mailed Jan. 29, 2010", 12 pgs.

"U.S. Appl. No. 11/745,105, Final Office Action mailed Mar. 30, 2010", 9 pgs.

"U.S. Appl. No. 11/745,105, Response filed Jan. 19, 2010 to Non Final Office Action mailed Sep. 18, 2009", 12 pgs.

"U.S. Appl. No. 11/745,105, Response filed Jun. 22, 2009 to Restriction Requirement mailed May 21, 2009", 6 pgs.

"U.S. Appl. No. 11/745,105, Response filed Jul. 29, 2010 to Final Office Action mailed Mar. 30, 2010", 12 pgs.

"U.S. Appl. No. 11/745,105, Restriction Requirement mailed May 21, 2009", 6 pgs.

"European Application Serial No. 05815206.7, Response filed Apr. 19, 2010 to Communication Dec. 18, 2009", 27 pgs.

"European Application Serial No. 05815215.8, Response filed Mar. 19, 2010 to Communication mailed Dec. 18, 2009", 12 pgs.

"European Application Serial No. 05817448.3, Response filed Mar. 19, 2010 to Communication mailed Dec. 18, 2009", 9 pgs.

"European Application Serial No. 07759589.0, Office Action mailed Feb. 18, 2010", 3 pgs.

"European Application Serial No. 07759589.0, Response filed Jun. 24, 2010 to Office Action mailed Feb. 18, 2010", 6 pgs.

"U.S. Appl. No. 11/316,120, Response filed Mar. 25, 2011 to Final Office Action mailed Oct. 28, 2010", 8 pgs.

"U.S. Appl. No. 12/910,106, Non Final Office Action mailed Apr. 4, 2011", 9 pgs.

"Japanese Application Serial No. 2007-538087, Office Action mailed Apr. 11, 2011", (w/ English Translation), 5 pgs.

"Japanese Application Serial No. 2007-538089, Office Action mailed Mar. 3, 2011", (w/ English Translation), 6 pgs.

"U.S. Appl. No. 10/971,550, PTO Response to 312 Amendment mailed Apr. 6, 2009", 2 pgs.

"U.S. Appl. No. 11/318,120, Decision on Pre-Appeal Brief Request mailed Apr. 19, 2011", 2 pgs.

"U.S. Appl. No. 11/316,120, Notice of Ailowance mailed Jul. 20, 2011", 7 pgs.

"U.S. Appl. No. 11/316,120, Pre-Appeal Brief Request filed Mar. 25, 2011", 5 pgs.

"U.S. Appl. No. 11/316,120, Supplemental Notice of Allowance mailed Sep. 1, 2011", 4 pgs.

(56) References Cited

OTHER PUBLICATIONS

"U.S. Appl. No. 11/394,601, Decision on Pre-Appeal Brief Request mailed Oct. 6, 2010", 2 pgs.
"U.S. Appl. No. 11/490,576, Pre-Appeal Brief Request filed May 12, 2011", 5 pgs.
"U.S. Appl. No. 11/745,105, Non Final Office Action mailed May 11, 2011", 13 pgs.
"U.S. Appl. No. 12/361,884, Preliminary Amendment filed Jun. 30, 2011", 12 pgs.
"U.S. Appl. No. 12/361,884, Supplemental Preliminary Amendment filed Jul. 27, 2011", 12 pgs.
"U.S. Appl. No. 12/365,428, Non Final Office Action mailed Aug. 31, 2011", 9 pgs.
"U.S. Appl. No. 12/910,106, Response filed Aug. 2, 2011 to Non-Final Office Action mailed Apr. 4, 2011", 14 pgs.
"European Application Serial No. 07759589.0, Summons to Attend Oral Proceedings mailed May 17, 2011", 3 pgs.
"Japanese Application Serial No. 2007-538087, Response filed Jun. 27, 2011 to Office Action dated Apr. 11, 2011", (w/ English Translation of Amended Claims), 12 pgs.
"Japanese Application Serial No. 2007-538088, Office Action mailed Jun. 13, 2011", (w/ English Translation), 5 pgs.
"Japanese Application Serial No. 2007-538088, Response filed Aug. 25, 2011 to Office Action dated Jun. 13, 2011", (w/ English Translation of Amended Claims), 9 pgs.
"Japanese Application Serial No. 2007-538089, Response filed May 25, 2011 to Office Action mailed Mar. 3, 2011", (w/ English Translation of Amended Claims), 8 pgs.
"U.S. Appl. No. 11/490,576, Decision on Pre-Appeal Brief Request mailed Aug. 30, 2011", 2 pgs.
"U.S. Appl. No. 11/490,576, Non Final Office Action mailed Nov. 9, 2011", 8 pgs.
"U.S. Appl. No. 11/490,576, Notice of Allowance mailed Jun. 4, 2012", 8 pgs.
"U.S. Appl. No. 11/490,576, Response filed Apr. 9, 2012 to Non Final Office Action mailed Nov. 9, 2011", 11 pgs.
"U.S. Appl. No. 11/683,584, Notice of Allowance mailed Aug. 7, 2012", 6 pgs.
"U.S. Appl. No. 11/745,105, Non Final Office Action mailed Feb. 7, 2012", 12 pgs.
"U.S. Appl. No. 11/745,105, Notice of Allowance mailed Aug. 20, 2012", 5 pgs.
"U.S. Appl. No. 11/745,105, Notice of Allowance mailed Oct. 31, 2011", 5 pgs.
"U.S. Appl. No. 11/745,105, Response filed Aug. 6, 2012 to Non Final Office Action mailed Feb. 7, 2012", 11 pgs.
"U.S. Appl. No. 11/745,105, Response filed Sep. 12, 2011 to Non-Final Office Action mailed May 11, 2011", 13 pgs.
"U.S. Appl. No. 12/361,884, Advisory Action mailed Sep. 10, 2012", 3 pgs.
"U.S. Appl. No. 12/361,884, Examiners Interview Summary mailed Oct. 1, 2012", 3 pgs.
"U.S. Appl. No. 12/361,884, Final Office Action mailed Jul. 3, 2012", 17 pgs.
"U.S. Appl. No. 12/361,884, Non Final Office Action mailed Oct. 12, 2011", 15 pgs.
"U.S. Appl. No. 12/361,884, Response filed Apr. 12, 2012 to Non Final Office Action mailed Oct. 12, 2011", 21 pgs.
"U.S. Appl. No. 12/361,884, Response filed Aug. 28, 2012 to Final Office Action mailed Jul. 3, 2012", 18 pgs.
"U.S. Appl. No. 12/361,884, Response filed Oct. 3, 2012 to Final Office Action mailed Jul. 3, 2012", 18 pgs.
"U.S. Appl. No. 12/365,428, Notice of Allowance mailed Feb. 22, 2012", 7 pgs.
"U.S. Appl. No. 12/365,428, Response filed Jan. 30, 2012 to Non Final Office Action mailed Aug. 31, 2011", 15 pgs.
"U.S. Appl. No. 12/910,106, Notice of Allowance mailed Jan. 26, 2012", 6 pgs.
"U.S. Appl. No. 12/910,106, Notice of Allowance mailed Oct. 27, 2011", 5 pgs.
"U.S. Appl. No. 13/476,599, Non Final Office Action mailed Aug. 30, 2012", 6 pgs.
"U.S. Appl. No. 11/549,352, Appeal Decision mailed Jul. 17, 2012", 9 pgs.
"European Application Serial No. 05815206.7, Office Action mailed May 16, 2012", 5 pgs.
"European Application Serial No. 05815206.7, Office Action mailed Sep. 12, 2012", 27 pgs.
"European Application Serial No. 05817448.3, Office Action mailed May 16, 2012", 5 pgs.
"European Application Serial No. 05817448.3, Response filed Sep. 14, 2012 to Office Action mailed May 16, 2012", 14 pgs.
"European Application Serial No. 06790023.3, Office Action mailed Jul. 16, 2008", 2 pgs.
"European Application Serial No. 06790023.3, Response filed Aug. 20, 2008 to Office Action mailed Jul. 16, 2008", 17 pgs.
"European Application Serial No. 06790023.3, Response filed Sep. 14, 2009 to Office Action mailed Mar. 4, 2009", 11 pgs.
"European Application Serial No. 06825988.6, Office Action mailed Jul. 16, 2008", 2 pgs.
"European Application Serial No. 06825988.6, Response filed Aug. 20, 2008 to Office Action mailed Jul. 16, 2008", 26 pgs.
"European Application Serial No. 06825988.6, Response filed Sep. 14, 2009 to Office Action mailed Mar. 4, 2009.", 12 pgs.
"European Application Serial No. 06847612.6, Office Action mailed May 26, 2009", 3 pgs.
"European Application Serial No. 06847612.6, Office Action mailed Jul. 30, 2008", 2 pgs.
"European Application Serial No. 06847612.6, Office Action mailed Dec. 7, 2010", 4 pgs.
"European Application Serial No. 06847612.6, Response filed Apr. 12, 2011 to Office Action mailed Dec. 7, 2010", 5 pgs.
"European Application Serial No. 06847612.6, Response filed Sep. 9, 2008 to Office Action mailed Jul. 30, 2008", 4 pgs.
"European Application Serial No. 06847612.6, Response filed Oct. 26, 2009 to Office Action mailed May 26, 2009", 12 pgs.
"European Application Serial No. 06847612.6, Summons to Attend Oral Proceedings mailed Jun. 20, 2012", 3 pgs.
"European Application Serial No. 07759589.0, Written Submission filed Dec. 5, 2011 to Summons to Attend Oral Proceedings dated May 17, 2011", 16 pgs.
"European Application Serial No. 09709347.0, Office Action mailed Oct. 4, 2010", 1 pg.
"European Application Serial No. 09709347.0, Response filed Oct. 28, 2010 to Office Action mailed Oct. 4, 2010", 7 pgs.
"International Application Serial No. PCT/US2005/037977, International Preliminary Report on Patentability dated Apr. 24, 2007", 9 pgs.
"International Application Serial No. PCT/US2005/037977, International Search Report mailed Mar. 21, 2006", 4 pgs.
"International Application Serial No. PCT/US2005/037977, Written Opinion mailed Mar. 21, 2006", 8 pgs.
"International Application Serial No. PCT/US2005/037978, International Preliminary Report on Patentability dated Apr. 24, 2007", 13 pgs.
"International Application Serial No. PCT/US2005/037979, International Preliminary Report on Patentability dated Apr. 24, 2007", 9 pgs.
"International Application Serial No. PCT/US2006/033414, International Preliminary Report on Patentability mailed Jun. 19, 2008", 11 pgs.
"International Application Serial No. PCT/US2006/033414, International Search Report mailed Mar. 1, 2007", 5 pgs.
"International Application Serial No. PCT/US2006/033414, Written Opinion mailed Mar. 1, 2007", 9 pgs.
"International Application Serial No. PCT/US2006/040291, International Preliminary Report on Patentability mailed Jun. 19, 2008", 11 pgs.
"International Application Serial No. PCT/US2006/047553, International Preliminary Report on Patentability mailed Jul. 3, 2008", 8 pgs.
"International Application Serial No. PCT/US2006/047553, International Search Report mailed Jun. 20, 2007", 3 pgs.

(56) References Cited

OTHER PUBLICATIONS

"International Application Serial No. PCT/US2006/047553, Written Opinion mailed Jun. 20, 2007", 6 pgs.

"International Application Serial No. PCT/US2007/065376, International Preliminary Report on Patentability mailed Oct. 9, 2008", 10 pgs.

"International Application Serial No. PCT/US2007/065376, International Search Report mailed Dec. 14, 2007", 5 pgs.

"International Application Serial No. PCT/US2007/065376, Written Opinion mailed Dec. 14, 2007", 11 pgs.

"International Application Serial No. PCT/US2007/074125, International Preliminary Report on Patentability mailed Feb. 5, 2009", 9 pgs.

"International Application Serial No. PCT/US2007/074125, International Search Report mailed Dec. 6, 2007", 4 pgs.

"International Application Serial No. PCT/US2007/074125, Writen Opinion mailed Dec. 6, 2007", 8 pgs.

"International Application Serial No. PCT/US2007/074135, International Preliminary Report on Patentability mailed Feb. 5, 2009", 9 pgs.

"International Application Serial No. PCT/US2007/078405, International Preliminary Report on Patentability mailed Mar. 26, 2009", 9 pgs.

"International Application Serial No. PCT/US2009/000587 Written Opinion mailed Apr. 24, 2009", 8 pgs.

"International Application Serial No. PCT/US2009/000587, International Preliminary Report on Patentability mailed Aug. 19, 2010", 10 pgs.

"International Application Serial No. PCT/US2009/000587, International Search Report mailed Apr. 24, 2009", 7 pgs.

"International Application Serial No. PCT/US2009/000693, International Preliminary Report on Patentability mailed Aug. 19, 2010", 9 pgs.

"Japanese Application Serial No. 2007-538087, Office Action mailed Apr. 17, 2012", w/ English Translation, 8 pgs.

"Japanese Application Serial No. 2007-538087, Office Action mailed Oct. 5, 2011", (w/ English Translation), 14 pgs.

"Japanese Application Serial No. 2007-538087, Response filed Mar. 23, 2012 to Office Action mailed Oct. 5, 2011", (w/ English Translation of Claims), 9 pgs.

"Japanese Application Serial No. 2007-538087, Response filed Jul. 13, 2012 to Office Action mailed Apr. 17, 2012", (w/ English Translation of Amended Claims), 13 pgs.

"Japanese Application Serial No. 2007-538088, Notice of Final Rejection mailed Dec. 6, 2011", (w/ English Translation), 9 pgs.

"Japanese Application Serial No. 2007-538088, Response filed Mar. 27, 2012 to Final Office Action mailed Dec. 6, 2011", (w/ English Translation of Claims), 11 pgs.

"Japanese Application Serial No. 2008-544324, Office Action mailed May 22, 2012", (w/ English Translation), 5 pgs.

"Japanese Application Serial No. 2008-544324, Office Action mailed Nov. 22, 2011", (w/ English Translation), 5 pgs.

"Japanese Application Serial No. 2008-544324, Response filed Jan. 27, 2012", (w/ English Translation of Amended Claims), 10 pgs.

"Japanese Application Serial No. 2008-544332, Office Action mailed Nov. 29, 2011", (w/ English Translation), 5 pgs.

"Japanese Application Serial No. 2008-544332, Response filed Mar. 19, 2012 to Office Action mailed Nov. 29, 2011", (w/ English Translation of Claims), 9 pgs.

"Japanese Application Serial No. 2009-503252, Office Action mailed Mar. 21, 2012", (w/ English Translation), 9 pgs.

"Japanese Application Serial No. 2009-503252, Response filed Jun. 20, 2012 to Office Action mailed Mar. 21, 2012", (w/ English Claims), 9 pgs.

"Japanese Application Serial No. 2010-545866, Office Action mailed Jun. 5, 2012", (w/ English Translation), 5 pgs.

"Japanese Application Serial No. 2010-545866, Response filed Sep. 5, 2012 to Office Action mailed Jun. 5, 2012", (w/ English Translation of Amended Claims), 12 pgs.

"U.S. Appl. No. 11/394,601, Response filed Dec. 2, 2009 to Non-Final office Action mailed Sep. 2, 2009", 11 pgs.

"U.S. Appl. No. 11/745,070, Final Office Action mailed Dec. 11, 2009", 18 pgs.

"European Application Serial No. 05815206.7, Communication Dec. 18, 2009", 4 pgs.

"European Application Serial No. 05815215.8, Communication mailed Dec. 18, 2009", 2 pgs.

"European Application Serial No. 05817448.3, Communication mailed Dec. 18, 2009", 2 pgs.

"U.S. Appl. No. 11/683,577, Notice of Allowance mailed Mar. 5, 2013", 11 pgs.

"U.S. Appl. No. 13/476,599, Examiner Interview Summary mailed Dec. 31, 2012", 3 pgs.

"U.S. Appl. No. 13/476,599, Response filed Dec. 19, 2012 to Non Final Office Action mailed Aug. 30, 2012", 11 pgs.

* cited by examiner

CARDIAC STIMULATION USING LEADLESS ELECTRODE ASSEMBLIES

CROSS-REFERENCE TO RELATED APPLICATIONS

This application claims priority from U.S. Provisional Application No. 60/844,599, filed Sep. 13, 2006, and entitled "Cardiac Stimulation System Using Leadless Electrode Assemblies," the entire contents of which are incorporated herein by reference.

TECHNICAL FIELD

This document relates to systems and techniques that electrically stimulate cardiac tissue or other tissue using a stimulator that is not physically connected to a lead that extends into the heart.

BACKGROUND

Pacemakers provide electrical stimulus to heart tissue to cause the heart to contract and pump blood. Conventionally, pacemakers include a pulse generator that is implanted, typically in a patient's pectoral region just under the skin. One or more leads extend from the pulse generator and into chambers of the heart, most commonly in the right ventricle and the right atrium, although sometimes also into a vein over the left chambers of the heart. An electrode at a far end of the lead provides electrical contact to the heart tissue for delivery of the electrical pulses generated by the pulse generator and delivered to the electrode through the lead.

The conventional use of leads that extend from the pulse generator and into the heart chambers has various drawbacks. For example, leads have at their far ends a mechanism, such as tines or a "j-hook," that causes the lead to be secured to a tissue region where a physician positions the lead. Over time, the heart tissue becomes intertwined with the lead to keep the lead in place. Although this is advantageous in that it ensures the tissue region selected by the physician continues to be the region that is paced even after the patient has left the hospital, it can be problematic if it becomes necessary to move or remove the lead. For example, subsequent to initial implant, it may be determined that an alternate location is preferable for pacing. Similarly, leads can fail. Failed leads cannot always be left in the patient's body, as potential adverse reactions including infection, thrombosis, valve dysfunction, etc., may occur. As such, lead-removal procedures, which can be difficult, sometimes must be employed. The conventional use of leads also limits the number of sites of heart tissue at which electrical energy may be delivered. This is because leads are often positioned within cardiac veins, and multiple leads may block a clinically significant cross-sectional fraction of the vena cava and branching veins leading to the pacemaker implant.

Potential use of leads within the left chambers of the heart may present various difficulties. For example, a thrombus or clot may form on the lead or electrode, and high pumping pressure on the left side of the heart may eject the thrombus or clot into distal arteries feeding critical tissues, which may cause a stroke or other embolic injury. Thus, conventional systems for pacing the left side of the heart instead have threaded a pacing lead through the coronary sinus ostium in the right atrium and through the coronary venous system to a pacing site in a vein over a left heart chamber. While a single lead may occlude a vein over the left heart locally, other veins can sometimes compensate for the occlusion by delivering more blood to the heart. Nevertheless, multiple such leads positioned in veins can cause significant occlusion, particularly in veins such as the coronary sinus when multiple side-by-side leads are used.

There are several heart conditions that may benefit from pacing at multiple sites of heart tissue. One such condition is congestive heart failure (CHF). It has been found that CHF patients have benefited from bi-ventricular pacing—that is, pacing of both the left ventricle and the right ventricle in a timed relationship. Such therapy has been referred to as "resynchronization therapy." The conventional use of leads limits the number of sites of heart tissue at which electrical energy may be delivered. Similarly, catheters are presently used in the coronary venous system, primarily to pace the left ventricle from the veins. It is known that venous pacing is less efficient at treating CHF than is pacing from the inside wall of the left ventricle.

Wireless Pacing Electrodes (WPEs) have been proposed for the treatment of heart failure through resynchronization of contraction of the right and left ventricles, and for prevention of arrhythmias, including ventricular tachycardia and ventricular fibrillation. A significant issue to be considered in achieving a commercially practicable system is the overall energy efficiency of the implanted system. For example, the energy transfer efficiency of two inductively coupled coils decreases dramatically as the distance between the coils increases. In one example, the WPE contains a battery that is recharged from an antenna located outside the patient. In this implementation, the WPE battery stores only enough energy to pace the heart for a few days, and recharging occurs approximately daily. In another example, a battery-free WPE contains a capacitor with charge-holding capacity sufficient to pace the heart for one or several heartbeats. Energy is transmitted to the WPE from an implanted antenna located outside of the heart, and in patients where multiple WPEs are used, each WPE capacitor is recharged at each heartbeat. Because of the distance between the WPE and the antenna, the coupling between the two may be inefficient, and frequent recharging of an implanted controller that drives the antenna may be required.

SUMMARY

This document relates to leadless electrode assemblies that may electrically stimulate cardiac tissue from distributed locations within the heart.

In a first general aspect, a cardiac tissue excitation lead includes a flexible elongate lead body having a proximal end adapted to be inserted into an implantable pulse generator assembly and having a distal end adapted to be positioned within a heart. The cardiac tissue excitation lead also includes a lead conductor extending within the lead body, and a transmitter assembly located near the distal end of the lead body and electrically connected to the pulse generator assembly via the lead conductor to wirelessly transmit pacing control information and pacing energy from the transmitter assembly to an implanted leadless electrode assembly.

In selected embodiments, the transmitter assembly may include a coil wound around a ferrite core, and the wireless transmission of pacing control information and pacing energy may occur when the pulse generator assembly supplies a time-varying current to the coil through the lead conductor to emit a magnetic field. The transmitter assembly may include an ultrasonic transducer, and the wireless transmission of pacing control information and pacing energy may occur when the pulse generator assembly supplies an electrical current to the ultrasonic transducer through the lead conductor to emit an ultrasonic beam. The transmitter assembly may include a pair of separated electrodes, and the wireless transmission of pacing control information and pacing energy may occur when the pulse generator assembly supplies a time-varying current through the lead conductor across the pair of separated electrodes to emit an electric field. The pacing control information may include pace timing information and a pace trigger signal. The cardiac tissue excitation lead may also include a first magnet positioned near the transmitter assembly that magnetically attracts a second magnet included with the leadless electrode assembly to orient the transmitter assembly and the leadless electrode assembly, and to maintain a fixed and minimal separation between the transmitter and leadless electrode assembly. The transmitter assembly may include a plurality of transmitter assemblies located near the distal end of the lead body that are electrically connected to the pulse generator assembly via the one or more lead conductors to wirelessly transmit pacing control information and pacing energy to a plurality of implanted leadless electrode assemblies. Each of the transmitter assemblies in the plurality of transmitter assemblies may transmit pacing control information and pacing energy to a different implanted leadless electrode assembly in the plurality of implanted leadless electrode assemblies.

In another general aspect, an implantable cardiac tissue excitation system includes an implantable pacing controller unit that includes a pulse generation circuit. The implantable cardiac tissue excitation system also includes a lead that includes a lead body extending between a proximal lead end attachable to the pacing controller unit and a distal lead end configured to be implanted within a heart. The lead also includes a lead conductor extending within the lead body. The implantable cardiac tissue excitation system further includes a transmitter assembly located near the distal lead end that is electrically connected to the pulse generation circuit through the lead conductor to wirelessly transmit pacing control information and charge energy from the transmitter assembly when the pulse generation circuit provides an electrical current to the transmitter assembly through the lead conductor. The implantable cardiac tissue excitation system further includes a leadless electrode assembly configured to be implanted within the heart and that includes a receiver to receive the wireless transmission from the lead transmitter assembly, a charge storage unit to store the charge energy, and an electrical stimulation circuit to deliver an electrical stimulus to cardiac tissue using the pacing control information and the charge energy.

In selected embodiments, the pacing controller may pass a time-varying current through the transmitter to generate an electric field to transmit the pacing control information and charge energy. The transmitter may include a coil enclosing at least a portion of a ferrite core and the pacing controller may pass a time-varying current through the coil to generate a magnetic field to transmit the pacing control information and charge energy. The transmitter may include a magnetic coil, the leadless electrode assembly may include a magnet, and a magnetic force between the magnetic coil and the magnet may assist in orienting the leadless electrode assembly. The implantable cardiac tissue excitation system may also include one or more implanted remote pacing stimulators in communicable contact with the leadless electrode assembly. Each of the one or more remote pacing stimulators may be located in the heart and may be configured to apply pacing stimuli to surrounding heart tissue at the direction of the leadless pacing module. The one or more remote pacing stimulators may communicate with the leadless electrode assembly wirelessly or over a wire between the leadless electrode assembly and the remote pacing stimulator. The leadless electrode assembly may also include a sense circuit for sensing electrical cardiac activity and a transmitter for wirelessly transmitting information associated with the sensed electrical cardiac activity. The implantable cardiac tissue excitation system may also include a magnet assembly configured to be affixed to a heart wall that includes a magnet that attracts a magnet included in the leadless assembly to position the leadless electrode assembly.

In another general aspect, a method of operating a cardiac pacing system includes transmitting an energy signal wirelessly from a wired lead whose distal end is positioned within a heart. The method also includes receiving the transmitted energy signal at a wireless pacing electrode assembly positioned within the heart. The method further includes issuing a pacing pulse from the wireless pacing electrode assembly.

In selected embodiments, the energy transmission may include charging energy and pacing information. Transmitting the energy signal wirelessly from the wired lead may include generating an electric field created at the wired lead, generating a magnetic field created at the wired lead, or generating an ultrasonic beam at the wired lead positioned in the first chamber of the heart. A plurality of wireless pacing electrode assemblies may receive the transmitted energy signal. The distal end of the wired lead may be positioned in a first chamber of the heart, and the wireless pacing electrode may be positioned in a second, different chamber of the heart. The first chamber may be a right ventricle of the heart and the second chamber may be a left ventricle of the heart.

In another general aspect, a method of operating a cardiac pacing system includes transmitting an energy signal wirelessly from a wired lead whose distal end is positioned in first chamber of a heart. The method also includes receiving the transmitted energy signal at a wireless pacing electrode assembly positioned within a second chamber of the heart. The method further includes issuing, in response to receiving the transmitted energy signal, a pacing pulse from the wireless pacing electrode assembly to surrounding cardiac tissue unless a native cardiac electrical signal is sensed by the wireless pacing electrode assembly within a specified time period from the receipt of the transmitted signal.

In selected embodiments, the energy transmission may include charging energy and pacing information. The wireless pacing electrode assembly may include sense circuitry to sense the native cardiac electrical signal. Transmitting the energy signal wirelessly from the wired lead may include generating an electric field created at the wired lead, generating a magnetic field created at the wired lead, or generating an ultrasonic beam at the wired lead implanted in the first chamber of the heart. The native cardiac electrical signal may originate at a sino-atrial node of the heart.

Advantages of the systems and techniques described herein may include any or all of the following: pacing at multiple sites may be beneficial where heart tissue through which electrical energy must propagate is scarred or dysfunctional, as this condition may halt or alter the propagation of an electrical signal through that heart tissue. In these cases, multiple-site pacing may be useful to restart the propagation of the electrical signal immediately downstream of the dead or sick tissue area. Synchronized pacing at multiple sites on the heart may inhibit the onset of fibrillation resulting from slow or aberrant conduction, which may reduce the need for implanted or external cardiac defibrillators. Additional advantages of wireless left-side pacing may include reduction of risk of stroke and improvement of left ventricle response by optimal stimulator positioning. Pacing thresholds may be reduced with distributed electrode surfaces on the seeds, left ventricle intra-wall positions, and adjacent Purkinje locations. Distributed electrode pacing sites, such as distributed left ventricle sites, may permit the heart to be defibrillated at lower energies than were previously realizable.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

This document describes various configurations of systems that employ leadless electrode assemblies to provide pacing therapy to cardiac tissues. The configurations and methods described in this document may permit efficient energy transfer between leaded transmitting devices and leadless electrode assemblies capable of providing pacing therapy to cardiac tissues. In some implementations, the leadless electrode assemblies may be capable of sensing and collecting information pertaining to local cardiac environments, and may be capable of transmitting the information for receipt by a leaded receiver, another leadless assembly, or by a pacing controller. Such information may be useful for a pacing controller or a physician.

Figure 1:
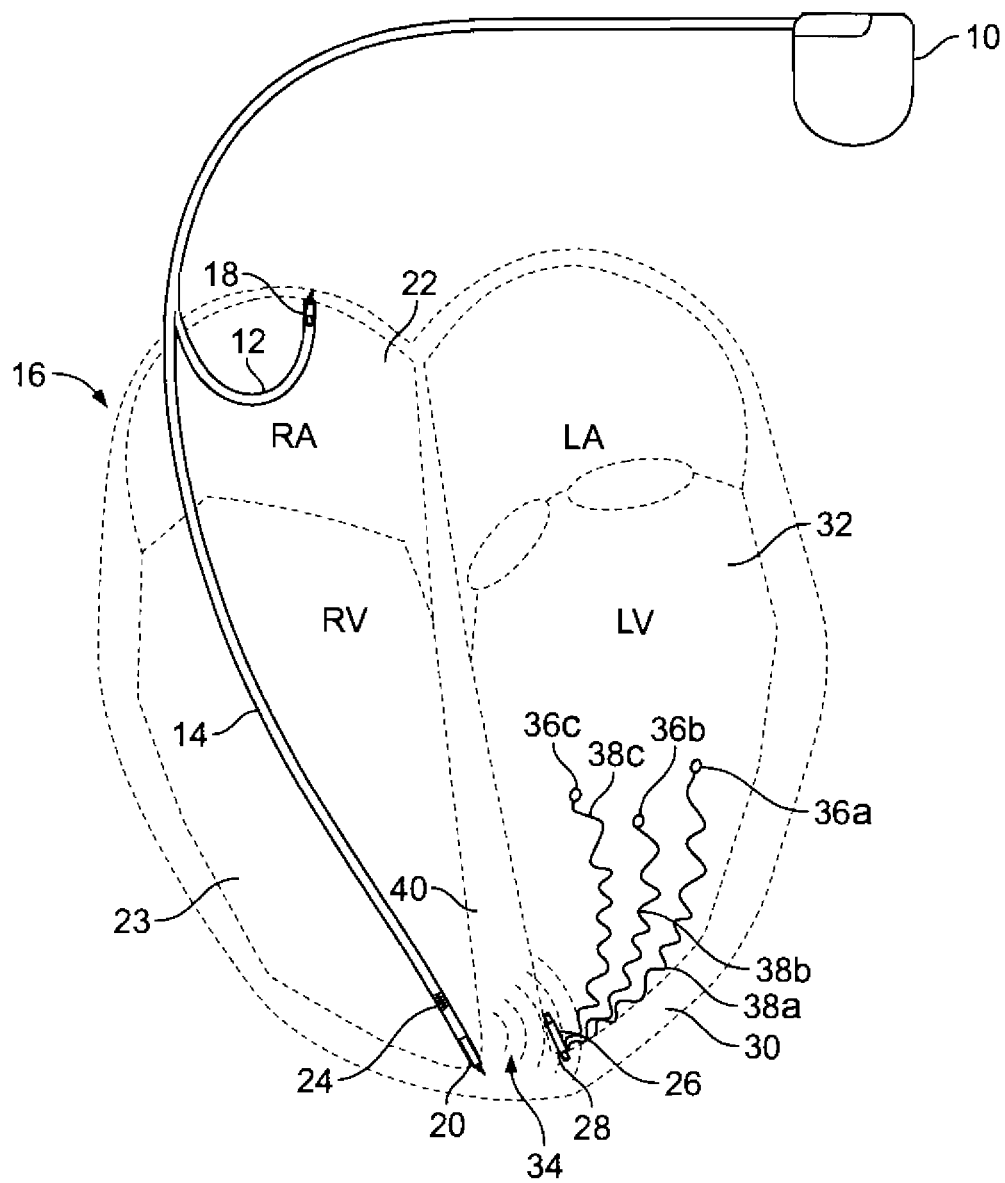
FIGS. 1-3 are diagrams of a heart and exemplary cardiac stimulation systems using leadless electrode assemblies implanted in or near the heart.
Figure 2:
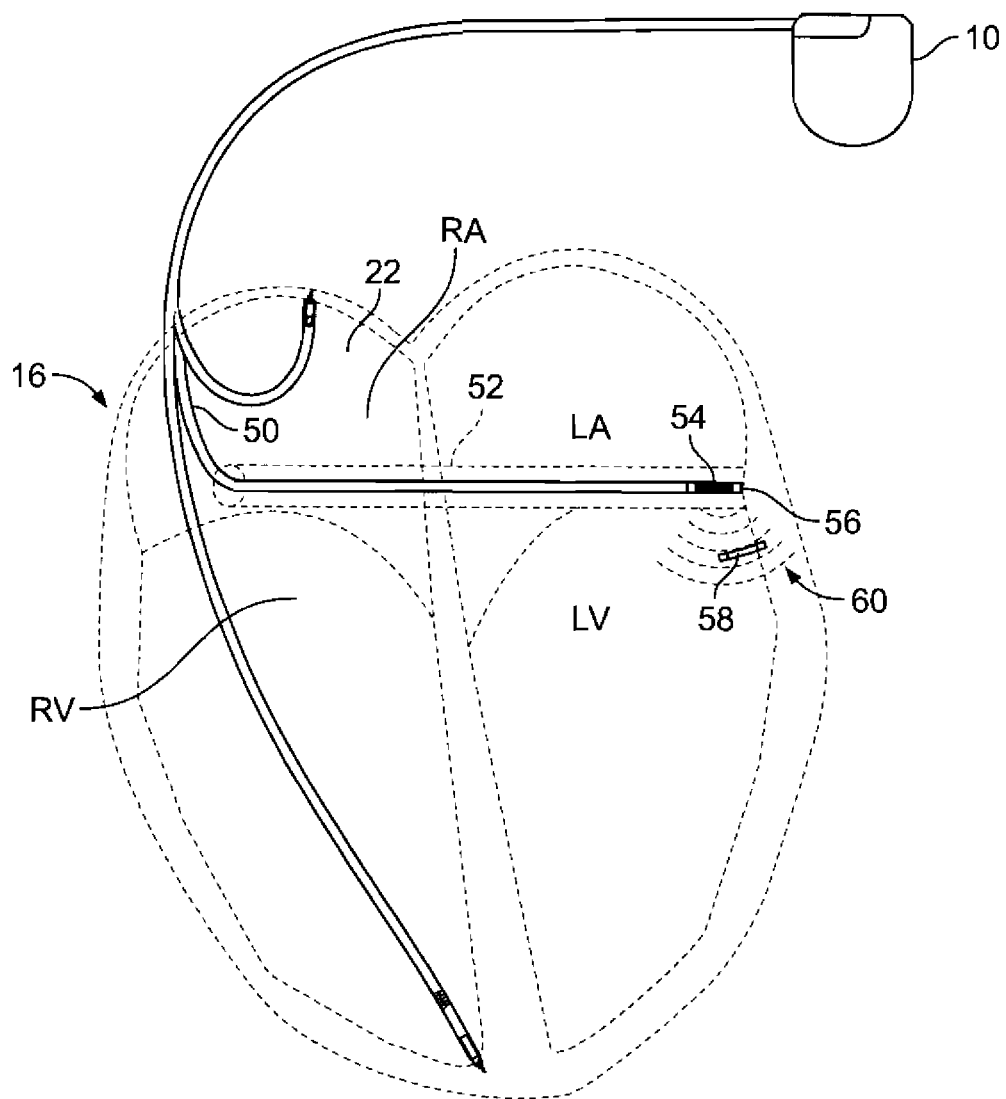
Figure 3:
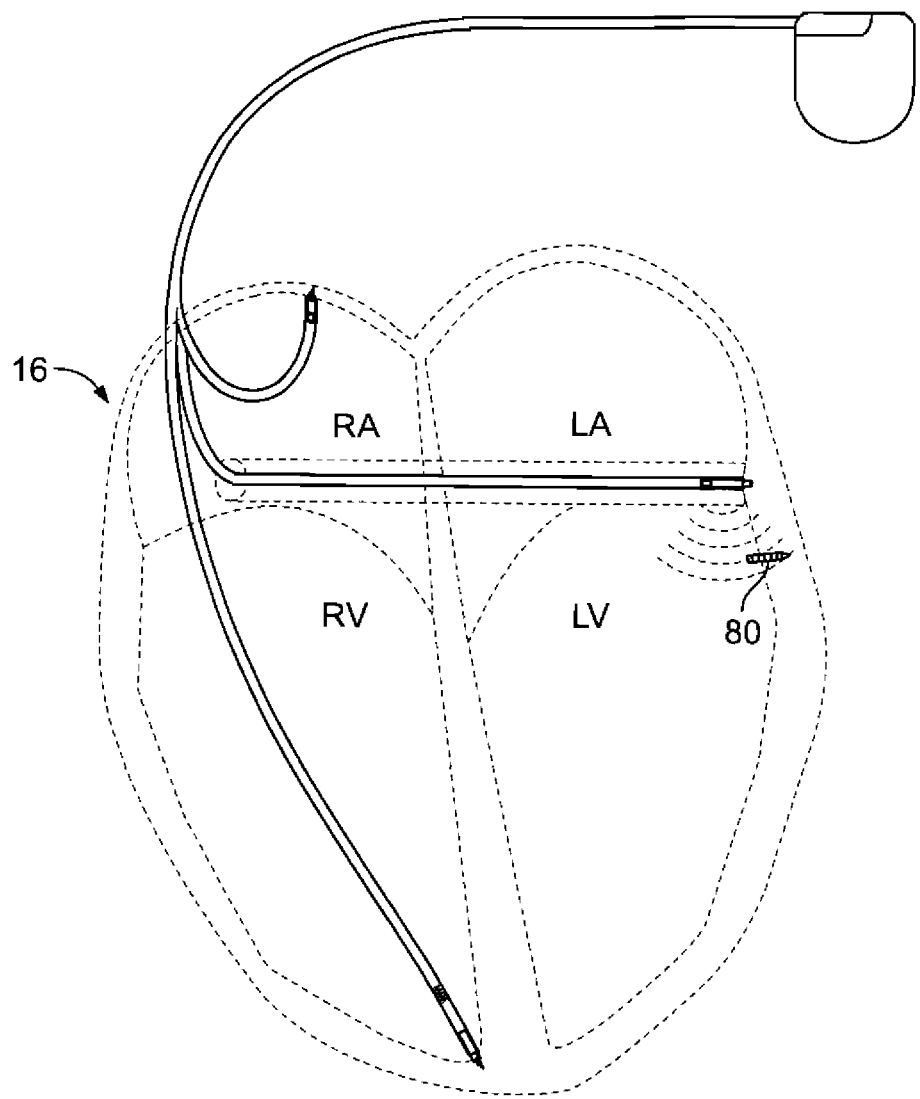

FIGS. 1-3 are diagrams of a heart 16 and exemplary cardiac stimulation systems using leadless electrode assemblies implanted in or near the heart 16. Referring first to FIG. 1, a pacing controller 10, such as an implantable defibrillator or pacemaker, is shown having two leads 12, 14 extending from the pacing controller 10 and entering a right atrium 22 of the heart 16. Each lead 12, 14 includes a flexible elongate lead body having a proximal end and a distal end, and a lead conductor extending within the lead body that is electrically connected to the pacing controller 10 at the proximal end. The distal end 18 of lead 12 is positioned in the right atrium 22, and hence lead 12 may be referred to as a right atrium lead.

The distal end of lead 14 is positioned in a right ventricle 23 of the heart 16, and hence lead 14 may be referred to as a right ventricle lead. In other implementations, leads may be positioned in other chambers of the heart, such as the left heart chambers.

Lead 14 passes through the right atrium 22 and enters the right ventricle 23 and may include a defibrillation coil electrode 24 that may be used to sense electrical activity in the right ventricle, and to supply a defibrillation shock through the heart to pulse generator 10 and/or right atrium lead 18. A transmitter 20, at the distal end of lead 14, transmits energy or information to one or more leadless electrode assemblies, such as leadless electrode assembly 26. Herein, the leadless electrode assembly 26, or wireless electrode assembly, may be referred to simply as a "seed." In some implementations, the pacing controller may communicate with the seed 26 by transmitting charge energy, pacing information, or both, through a lead, such as lead 14, to be received by the seed 26.

In one implementation, the seed 26 has an internal receiver that may receive communications and/or energy from transmitter 20. In an implementation, the pacing controller 10 includes a pulse generator that supplies an appropriate time-varying current to the transmitter 20. The seed 26 may include an electrical charge storage that may be charged by the received energy transmission from the leaded transmitter, and may also have a triggering mechanism to deliver stored electrical charge to adjacent heart tissue. In this fashion, pacing stimuli may be delivered to cardiac tissue remote from the cardiac lead, which may advantageously permit cardiac rhythms to be more effectively managed, and may permit a level of cardiac stimulation coverage using fewer cardiac leads. In an exemplary implementation, the wireless electrode assembly 26 includes a capacitor to store received electrical charge. In another implementation, the wireless electrode assembly 26 includes a battery to store received electrical charge.

Seed 26 is shown endocardially affixed via a helical tine 28 to a wall 30 of a left ventricle 32 of the heart 16. Transmitter 20 may transmit charge energy and data, such as pace trigger signals, pacing amplitude information, and pulse width information to the seed 26 via RF transmissions 34, according to some implementations. In this manner, the seed 26 may receive energy and communications from the pacing controller 10 through the transmitter 20. As just described, the transmitter 20 and the connected pacing controller 10 together, or the pacing controller 10 or transmitter 20 individually, may be referred to as a transmitter, while the wireless electrode assembly 26 may be referred to as a receiver. While only one seed 26 is shown in FIG. 1, additional seeds 26 may be located throughout any of the chambers of the heart 16, such as the left ventricle, right ventricle, left atrium or right atrium, and each may receive energy or information from the pacing controller 10 through RF or ultrasonic transmissions, whether through transmitter 20 on lead 14, or through a transmitter attached to other leads (not shown in FIG. 1). In one implementation, the pacing controller 10 may transmit, and the seed 26 may receive, 1) a charging signal to charge an electrical charge storage device contained within the seed 26 by inductive coupling, and 2) an information signal, such as a pacing trigger signal, pacing amplitude information and/or pacing pulse width information that is communicated to a selected one or more of the seeds 26, commanding that seed to deliver its stored charge to the adjacent or surrounding cardiac tissue.

Generally, the pacing controller 10 may include circuitry to sense and analyze the heart's electrical activity, and to determine if and when a pacing electrical pulse should be delivered, and by which of the seeds 26. The sensing capability may be made possible by having sense electrodes included within the physical assembly of the pacing controller 10. Alternatively, the seed 26 may sense local cardiac activity, and may communicate this information to the pacing controller 10. This may occur, for example, by wireless transmission of the information from the seed directly to a receiving circuit at the pacing controller 10 in some implementations, or alternatively by wireless transmission from the seed to a receiver on a cardiac lead, such that the information may then be conveyed over a lead conductor to the pacing controller. In some implementations, the seed 26 is not provided with sensing capability, and may not be equipped with the capability of transmitting information to the pacing controller 10 (for example, to communicate information about sensed electrical events). In alternative implementations, the seeds 26 may communicate sensed information to each other, either by wired or wireless connection.

An external programmer (not shown) may be used to communicate with the pacing controller 10, including after the pacing controller 10 has been implanted. The external programmer may be used to program such parameters as the timing of stimulation pulses in relation to certain sensed electrical activity of the heart, the energy level of stimulation pulses, the duration of stimulation pulses (that is, pulse width), etc. Additional information such as locations of seeds 26 within heart chambers may be programmed, as well as pacing requirements involving one or more of the distributed seeds 26. The programmer may include an antenna to communicate with the pacing controller 10, using, for example, RF signals. The implantable pacing controller 10 may accordingly be equipped to communicate with the external programmer using, for example, RF signals. Similarly, the pacing controller 10 may transmit information, such as sensed cardiac patient information, system status information, warning information, and the like, to an external computing device. Physicians or care providers may then monitor the information and make changes as appropriate.

Because the seed assembly 26 may receive charge energy via RF transmissions, the seed assembly 26 may be constructed without a battery in some implementations, which may permit the seed assembly 26 to be advantageously small. This may make seed implantation easier and permit pacing at sites that might not otherwise be possible with larger assemblies that include a battery. In one implementation, the seed assembly 26 includes a capacitor that may be charged by energy received from the pacing controller 10 through transmitter 20 via RF or ultrasonic transmissions. In an implementation, the pacing controller 10 may send pulses to the transmitter 20 at an RF frequency of about 150 KHz. The seed electrode assembly 26 may then provide pacing therapy to surrounding cardiac tissue using the received energy and communication information.

In some implementations, one or more additional electrode assemblies 36 may be positioned at appropriate pacing sites, and may be electrically connected to the seed electrode assembly 26 via micro lead wires 38. As shown in FIG. 1, the additional electrode assemblies 36 are screw-in electrodes affixed to the left ventricle wall. The seed electrode assembly 26 may pass charge energy, communications data, or both to the electrode assemblies 36 over the micro leads 38, including energy or communications received wirelessly from the pacing controller 10 through the transmitter 20. The additional electrode assemblies 36 may then provide pacing stimulation to surrounding cardiac tissue. In this manner, cardiac synchronization may be improved as additional pacing sites over a larger area may be realized in a coordinated fashion. Transmission efficiency may be maintained, despite the large pacing coverage area, because of the relative proximity of the wireless transmitter on the lead and the wireless receiver at the seed, as will be described more fully below. While the additional electrode assemblies 36 are shown connected to the seed electrode assembly 26 via micro leads 38, in other implementations the additional electrode assemblies may wirelessly communicate with the seed electrode assembly or with the pacing controller 10 (through transmitter 20, for example), permitting the micro leads 38 to be omitted.

As seen in FIG. 1, the transmitter 20 may be positioned in an approximately parallel orientation with respect to the wireless seed assembly 26 to facilitate efficient coupling, according to an implementation. Many other orientations are possible. For example, the transmitter 20 may abut a septal wall 40 of the right ventricle 23, and the wireless seed assembly 26 may be placed on the septum of the left ventricle parallel to the septal wall 40 of the right ventricle 23. Transmitter 20 may be oriented approximately parallel to the seed assembly 26 in some implementations, but other orientations are possible.

Efficient coupling may be realized using configurations disclosed in this document because of the relatively close proximity with which transmitter and receiver may be positioned. In one implementation, both transmitter 20 and the receiver in seed 26 consist of coils of wire wound around permeable cores. Tight coupling between transmitter and receiver (which may be viewed as a toroidal transformer with two gaps) means that signals received from the transmitter may be large compared to signals received from extraneous external sources, thus helping reduce the problem of interference. This may provide robust system operation, and may minimize instances of system malfunction. Energy may be efficiently coupled to the seed 26, where it may be stored on a capacitor located within the seed 26. Pacing instructions may be communicated from a controller housed in the pacing controller 10 and transmitted to the seed 26 to control firing of the septal and free wall electrodes 36, in this example. In implementations where seeds can sense cardiac signals and wirelessly transmit, voltages sensed at the seed 26 and additional electrode assemblies 36 can be efficiently coupled back to the transmitter coil 20 for use by the pacing controller 10 in determining the timing of pacing on each lead.

Referring now to FIG. 2, a third lead 50 is shown. Like the leads 12, 14 shown in FIG. 1, lead 50 is electrically connected to the pacing controller 10 at the lead's proximate end by a lead conductor that extends within a lead body. Lead 50 extends through the right atrium 22 and into a coronary sinus 52, where a transmitter 54 near a distal end 56 of the third lead 50 is positioned within the coronary sinus 52. In similar fashion to the system shown in FIG. 1 and described above, the transmitter 54 may transmit pacing energy or communication data, received from the pacing controller 10, to a left ventricle wireless electrode assembly 58 via RF or ultrasonic transmissions 60.

The system shown in FIG. 3 is similar to the system of FIG. 2, but includes an alternative style wireless electrode assembly 80. Like the system shown in FIG. 1, the systems shown in FIGS. 2-3 provide efficient coupling between transmitter and receiver because of the close proximity with which transmitter and receiver are positioned. Various implementations of seed assemblies 26, including those shown in FIGS. 1-3, will now be described with reference to FIG. 4.

Figure 4:
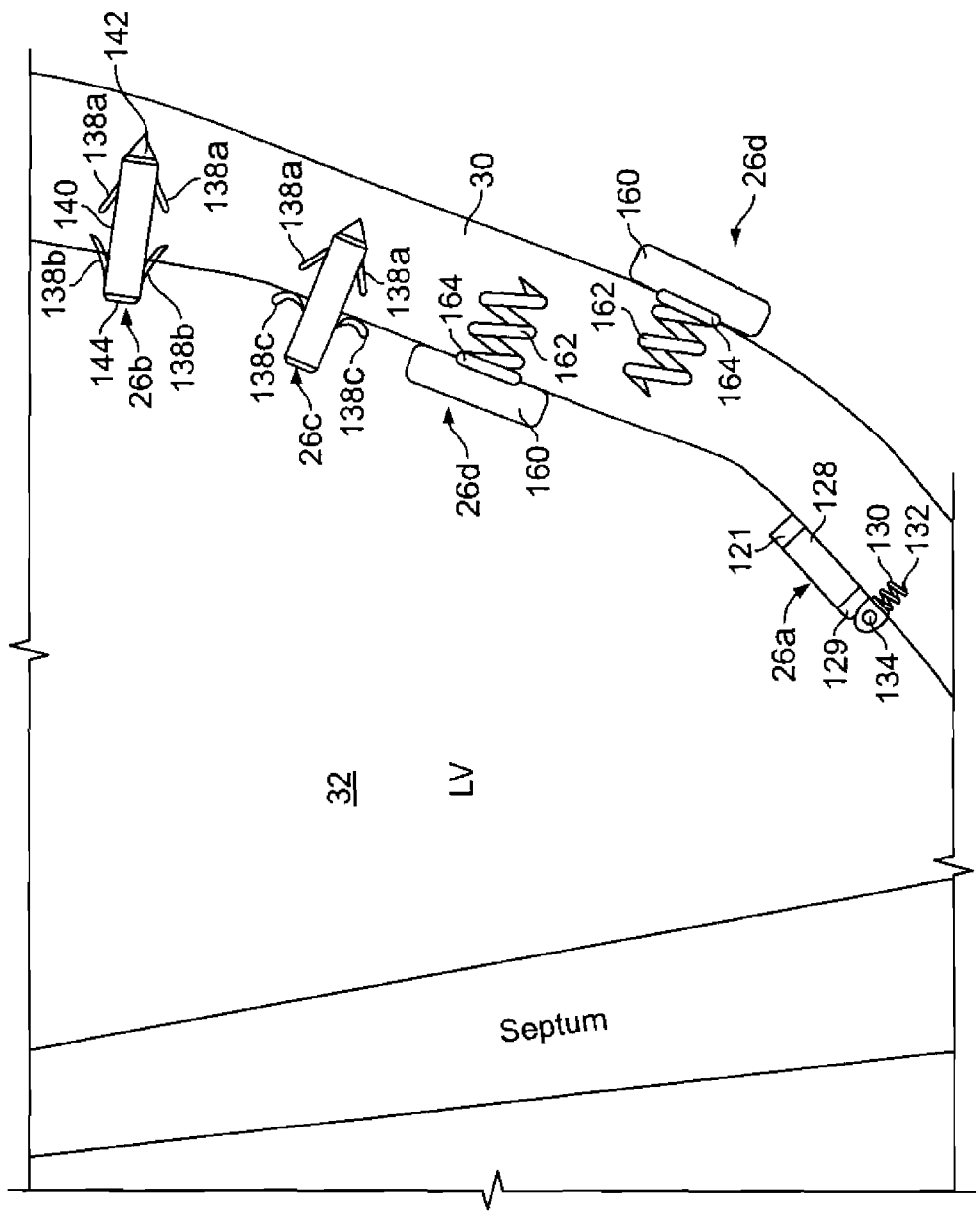
FIG. 4 is a diagram of various exemplary implementations of leadless electrode assemblies that may be used in the systems of FIGS. 1-3.

FIG. 4 is a diagram of various exemplary implementations of leadless electrode assemblies 26 that may be used in the systems of FIGS. 1-3. The leadless electrode assemblies 26 are attached to a wall of the heart—in this example, the wall 30 of the left ventricle 32. A first leadless (or wireless) electrode assembly 26a includes a proximal electrode 121 at or near a proximal end of the assembly 26a and a distal electrode 129 at or near a distal end of the assembly 26a, according to an implementation. The proximal electrode 121 and distal electrode 129 may provide bipolar electrode capabilities for the wireless electrode assembly 26a, thereby permitting the assembly 26a to supply an electrical charge between the proximal and distal electrodes 121 and 129 (and across the nearby heart tissue). The distal end of the wireless electrode assembly 26a may also include a fixation device 130, such as a helical tine, to secure the wireless electrode assembly 26a to the heart chamber wall 30. For example, a distal tip 132 of the helical tine 130 may engage the heart chamber wall 30 and, when a torque is applied to the wireless electrode assembly 26a, the helical tine 130 may screw through the endocardium (e.g., the inner lining of the heart chamber wall) and into the myocardium.

Such a configuration may permit the wireless electrode assembly 26a to be secured to the heart chamber wall 30. In some implementations, the fixation device 130 may also serve as at least a portion or all of the distal electrode 129. For example, the fixation device 130 may comprise an electrically conductive material (e.g., a metallic material or the like) and may be electrically connected to the distal electrode circuitry so as to serve as at least a portion of the distal electrode. This may permit the fixation device 130 to electrically stimulate the surrounding heart wall tissue (including the myocardium in some embodiments) when the wireless electrode assembly 26a is activated.

At least a portion of the wireless electrode assembly 26a may be pivotable relative to a portion of the fixation device 130. In the implementation depicted in FIG. 4, a body 128 of the wireless electrode assembly 26a is pivotable about a pin axis 134 relative to the fixation device 130. For example, the fixation device 130 may include a biasing portion (not shown) that is coiled around a pin (not shown) and presses against a portion of the electrode body 128, thereby applying a torque load so that the body 128 of the wireless electrode assembly 26a is pivotable about the pin axis 134 relative to the fixation device 130. A ratcheting mechanism may alternatively be used as the biasing portion.

According to an implementation, a physician may implant the leadless electrode assembly 26a using a delivery catheter. The wireless electrode assembly 26a may initially be arranged in the delivery catheter so that the biasing portion is in a loaded condition. In some implementations, the biasing portion is in the loaded condition when the fixation device 130 extends in a generally longitudinal direction from the body 128 of the wireless electrode assembly 26a. Thus, when the delivery catheter is retracted or otherwise separated from the wireless electrode assembly 26a, the biasing portion may press against an end face of the body 128 so as to urge the body 128 to pivot about the pin axis 134. The body 128 may pivot until it assumes a deployed position and contacts the heart wall 30 (see FIG. 4). In some implementations, the movement of the wireless electrode assembly 26a may be substantially reduced so that tissue may grow over and surround the wireless electrode assembly 26a over a period of days to weeks. In these implementations, the wireless electrode assembly 26a may be immobilized by the surrounding tissue to prevent future dislodgement. Tissue growth to surround a wireless electrode assembly 26 is not required for delivery of pacing stimuli to cardiac tissue, however. Generally, a wireless electrode assembly 26, such as any of the seeds 26 shown in FIGS. 1-4, may be capable of delivering pacing stimuli to adjacent, nearby, or surrounding cardiac tissue from the time of implantation.

Still referring to FIG. 4, a second leadless electrode assembly 26b is anchored to the inner wall surface of the left ventricle by fixation devices 138. The leadless electrode assembly 26b has a main body 140 that, in this example, is cylindrically shaped with a conical distal tip portion. The assembly 26b may include two bipolar electrodes 142 and 144 that are capable of providing an electrical stimulation pulse to nearby heart tissue. The distal electrode 142 is located along the distal end of the assembly 26b, and the proximal electrode 144 is located along a proximal end. The assembly 26b may include a fixation device in the form of opposing biased tines that are configured to extend outwardly away from the body 140 when released from a delivery catheter. In this example, the assembly 26b is anchored to the inner wall surface of the left ventricle by the fixation device 138 (e.g., one or more biased tines near the proximal electrode 144 and one or more opposing biased tines near the distal electrode 142). The fixation device 138 may include biased distal tines 138a that extend outwardly from the body of the assembly 26b after the distal portion of the body has penetrated through the endocardium and into myocardium tissue. The fixation device 138 may also comprise an opposing set of biased proximal tines 138b that extend outwardly from the body of the assembly 26b. When the opposing biased tines are arranged in such an operative position, the assembly 26b may remain embedded in the heart chamber wall. Following implantation and a healing period, at least a portion of the assembly 26b may be incorporated into the adjacent heart tissue. In some implementations, the opposing biased tines may retain the position of the assembly 26b so that the tissue may grow and eventually incorporate the assembly 26b therein, and may prevent the assembly 26b from unintentional dislodgement from the tissue.

A third leadless electrode assembly 26c is similarly anchored to the inner wall surface of the left ventricle, but uses an alternative fixation device 138. The assembly 26c includes biased distal tines 138a that extend outwardly from the body of the assembly 26c, and also hook-shaped biased proximal tines 138c that may rest against the inner wall surface of the left ventricle after implantation by a delivery catheter.

FIG. 4 also shows a pair of fourth wireless electrode assemblies 26d. The wireless electrode assembles 26d are mounted to the wall 30 of the left ventricle 32, one on the endocardial side (that is, inside the heart) and one on the epicardial side (that is, outside of the heart). The assemblies 26d include a "button-shaped" body 160, and are anchored to the wall 300 by helical tine fixation elements 162, which are attached to the seed body 160 at fixation point 164.

Each of the wireless electrode assemblies 26 shown in FIG. 4 may include a receiver to receive wireless RF transmissions from a transmitter on a cardiac lead, according to an implementation. As described previously, such transmissions can include pacing energy and pacing information. The assemblies 26 may each include two or more stimulation electrodes for providing electrical stimulation to cardiac tissue, and in some implementations may include two or more sense electrodes for sensing cardiac signals local to their implantation environment. In some implementations, the seeds 26 may measure voltages, for example, such as voltages associated with the heart's native conduction cycles or voltages associated with delivered pacing stimuli. In some implementations, the seeds 26 may contain a pressure sensor for measurement of blood pressure in the heart chamber. As described above, in some implementations the seeds 26 may include storage space for storing sensed or measured information and may further include a transmitter for wirelessly transmitting the information for use by the pacing controller 10. The assemblies 26 shown in FIG. 4 are exemplary, and variations are possible. For example, alternative fixation devices may be used, such as different hook, tine or screw arrangements.

FIGS. 5-8 are diagrams of exemplary systems of leaded transmitter assemblies and leadless receiver electrode assemblies. The transmitters and receivers may be coupled together to permit energy transfer and information sharing, as previously described, in several different ways, including magnetic field coupling, electric field coupling, and ultrasonic coupling. While the descriptions below focus, for simplicity, on leaded transmitter assemblies and leadless receiver assemblies, in some implementations the leadless assemblies may both transmit and receive information, and similarly for the leaded assemblies.

Figure 5:
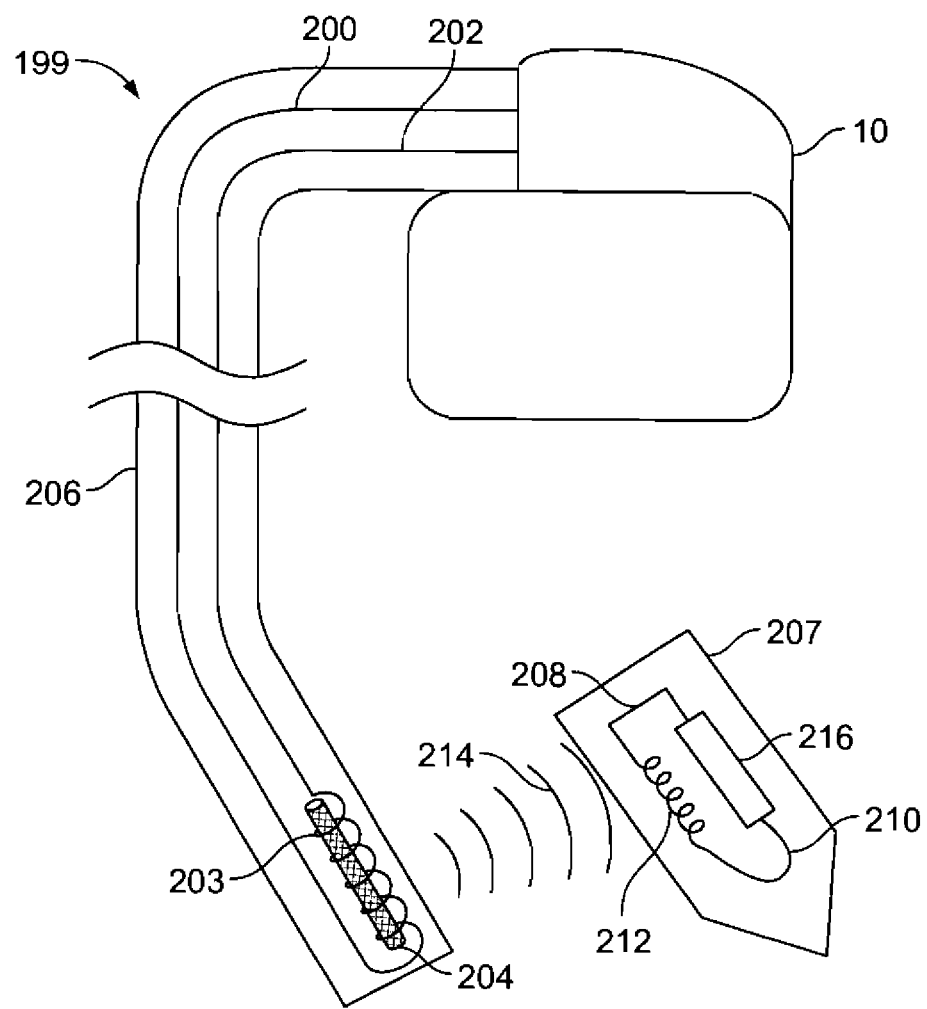
FIGS. 5-8 are diagrams of exemplary systems of leaded transmitter assemblies and leadless receiver electrode assemblies.

Referring first to FIG. 5, a diagram of an exemplary implementation that utilizes magnetic field coupling between a leadless electrode assembly and a leaded device is shown. For simplicity, a single lead 199 is shown attached to the pacing controller 10 in FIG. 5. Lead 199 may correspond to lead 14 of FIG. 1 or lead 50 of FIG. 2, and the distal end of lead 199 may be positioned, for example, in the right ventricle, the coronary sinus, outside of the left ventricle near an apex of the heart, or at some other appropriate location in or near the heart. As is conventional, lead 199 includes a protective and insulating shroud 206, or lead body, which may be flexible and elongate, according to an implementation. In this simplified example, lead 199 contains electrically isolated first and second lead conductors 200, 202, which are each independently electrically connected to the pacing controller 10 and also to a coil 203 near the distal end of lead 199. In an implementation, the first and second lead conductors 200, 202 may be referred to as a single lead conductor since collectively they provide a current path through the coil 203. The coil 203, in this example, is wound around a ferrite core 204, such that when time-varying current is passed from the pacing controller 10, through the first wire 200, through the coil 203, and back to the pacing controller 10 through the second wire 202, a magnetic field 214 is generated. Examples of time-varying current include alternating current (AC) or pulsed current.

Similarly, a wireless electrode assembly (seed) 207 includes two wires 208, 210, each connected to one end of a coil 212, which may be either internal or external to the seed 207. The wires 208 and 210 also are connected to a seed circuit 216 within the seed 207, which may include capability for charge storage, electrical stimulation (pace) delivery, electrical sense, and information transmit, receive and storage. Seed 207 may correspond to any of the seeds shown in FIGS. 1-4 and described above.

The seed coil 212 may be inductively coupled to the lead coil 203 to permit transmissions from the leaded transmitter to the leadless receiver, according to an implementation. A change in current flow through the lead coil 203, as by supplying a time-varying current from pacing controller 10, may produce a magnetic field 214 that induces current flow in the seed coil 212. The efficiency of magnetic energy transmission can be relatively high if there are no absorbers of energy that compete with the seed coil 212, and if the seed coil 212 is in the near field of the lead coil 203 (e.g., within a distance equal to about a few times the linear dimensions of lead coil 203). At sufficiently low frequencies, the magnetic field energy generated when current flows into lead coil 203 is returned to the power supply when the current flows back out of the lead coil 203, minus energy absorbed by the seed coil 212. Energy coupling efficiency may generally increase with frequency. However, at frequencies higher than several megahertz, two additional losses may occur—some energy may continue out into space in the form of radiation, and some energy may be absorbed by conductive tissues of the body that surround the lead coil 203. Energy coupling efficiency may drop rapidly when seed coil 212 is in the far field of lead coil 203, because the magnetic field decreases with the cube of distance from the lead coil 203 in its far field.

Energy coupling efficiency has a direct impact on the battery lifetime of pacing controller 10, and is directly proportional to battery lifetime when coupling losses dominate the controller energy budget. The geometry and magnetic properties of coils 212 and 203, as well as the operating frequency, can be tailored to optimize energy coupling efficiency for a given anticipated separation of the two coils 203 and 212. In an implementation, the two coils may be separated by a small distance (for example, a smallest distance allowable by human anatomy considerations) to optimize coupling efficiency and battery lifetime.

Each of coils 203 and 212 may be considered an antenna in a transmit and receive configuration. A receiving circuit within the seed circuit 216 may decode data transmissions received in this fashion. Similarly, a charge storage circuit within the seed circuit 216, such as a capacitor in one implementation, may store received charge energy received in the transmission. Two or more pacing electrodes (not shown in FIG. 5) at the seed 207 may electrically stimulate cardiac tissue proximate the seed implant location. For example, the seed may receive pacing energy and may store the energy on the capacitor, and may then receive a pacing trigger signal, which may trigger the seed to deliver the pacing energy in the form of a pacing stimulus to the proximate cardiac tissue through the two or more pacing electrodes. Alternatively, the pacing energy received from transmit coil 203 by receive coil 212 may be delivered directly to the proximate tissues through two or more electrodes on or near seed body 207. In this case, the incident energy may serve as a trigger signal to pace, and the width of the received burst of energy may be equal to the width of the pacing pulse. A diode may be included in circuitry 216 to rectify the AC voltage generated in coil 212, or the incident pulse magnetic field 212 may be shaped to provide an AC pulse at the seed electrodes that is adequate for pacing proximate tissue.

Figure 6A:
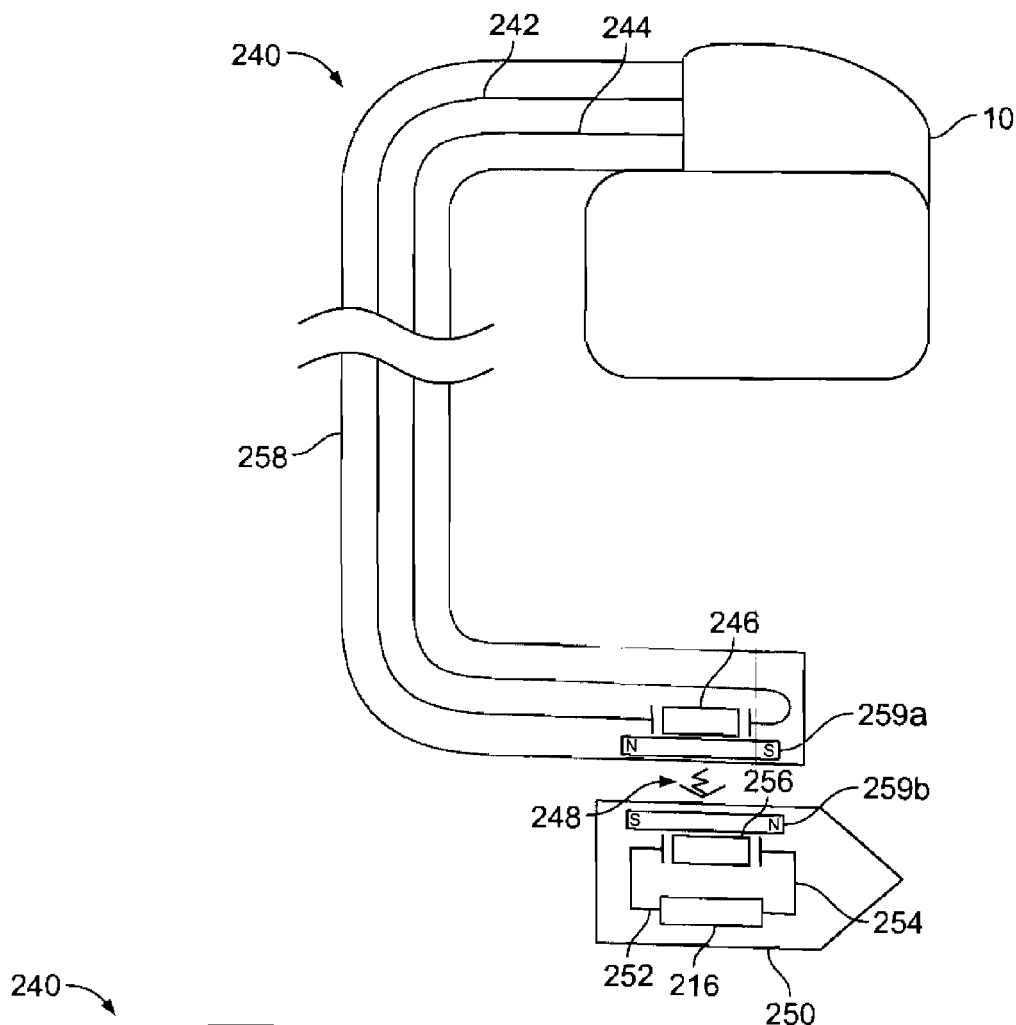

Turning now to FIG. 6A, a diagram of an exemplary implementation that utilizes ultrasonic coupling between a leadless electrode assembly and a leaded device is shown. For simplicity, a single lead 240 is shown attached to the pacing controller 10 in FIG. 6A. Lead 240 may correspond to lead 14 of FIG. 1 or lead 50 of FIG. 2, and the distal end of lead 240 may be positioned, for example, in the right ventricle, the coronary sinus, outside of the left ventricle near the apex of the heart, or at some other appropriate location in or near the heart. As is conventional, lead 240 includes a protective and insulating shroud 258, or lead body, which may be flexible and elongate, according to an implementation. In this simplified example, lead 240 contains electrically isolated first and second wires 242, 244, which are each connected to the pacing controller 10 and also to an ultrasonic transducer 246 near the distal end of the lead 240. In an implementation, the first and second lead conductors 242, 244 may be referred to as a single lead conductor since collectively they provide a current path through the transducer 246. The ultrasonic transducer 246 may be, for example, a piezoelectric crystal, such that when a pulse of current is passed from the pacing controller 10, through the first wire 242, through the transducer 246, and back to the pacing controller 10 through the second wire 244, the piezoelectric electric crystal may oscillate at a high frequency and produce sound waves that comprise an ultrasonic beam 248. Supplied current from the pacing controller 10 may include, for example, alternating current, pulsed direct current, or pulsed alternating current, depending upon the type of ultrasonic transducer used. In an implementation, the pacing controller 10 may appropriately supply current to the transducer 246 such that the transducer 246 generates an ultrasonic beam 248 having suitable resonant frequency for efficient energy and information transfer. The ultrasonic transducer 246 could alternatively be constructed from discrete components.

Similarly, a wireless electrode assembly (seed) 250 includes two conductors or wires 252, 254, each connected to one end of another ultrasonic transducer 256. Wires 252 and 254 also are connected to a seed circuit 216 within the seed 250, which may include capability for charge storage, electrical stimulation (pace) delivery, electrical sense, and information transmit, receive and storage. Seed 250 may correspond to any of the seeds shown in FIGS. 1-4 and described above. Ultrasonic coupling may provide an efficiency advantage because the beam produced upon transducer excitation may be more directed, permitting reduced loss when the receiving transducer is appropriately oriented relative to the transmitting transducer. Conversely, if the transmitted ultrasound beam only partially intersects receiver 256, the received energy may become too small to pace the tissue. The ultrasound energy transmission of FIG. 6A may thus be more orientation-dependent than the magnetic energy transmission of FIG. 5.

Figure 6B:
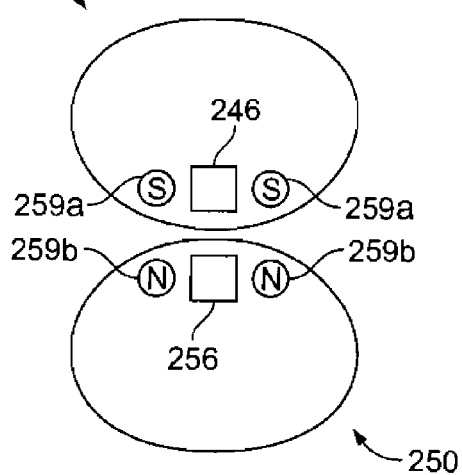

In an implementation of the configuration shown in FIG. 6A, permanent magnets 259 are included near the sites of transmitter 246 (magnet 259a) and receiver 256 (magnet 259b). The permanent magnets 259 may be aligned parallel to the lead and seed bodies, with opposite polarity on the lead and seed magnets for attraction. These magnets 259 may be placed at either end of transducers 246 and 256, or alongside the transducers. Multiple magnet configurations are possible. While the transducers 246, 256 are shown within the lead 240 and seed 250, respectively, the transducers 246, 256 (or a portion thereof, such as one or more surfaces of the transducer (s)) may be external to the lead 240 or seed 250, respectively. Seed circuit 216 may include the functionality described above with respect to the seed circuit of FIG. 5. FIG. 6B is an end view of the lead 240 and the seed 250 for an alternative implementation that includes magnets 259 on two sides of each of the transmitter 246 and receiver 256. As shown in FIG. 6B, two permanent magnets 259a are shown, each near opposite sides of the transmitter 246, and two permanent magnets 259b are similarly shown near opposite sides of the receiver 256. The configurations shown in FIG. 6A and FIG. 6B may permit the transmitter 246 and receiver 256 to be appropriately aligned, which may permit efficient energy transmission with minimal energy loss.

Figure 7A:
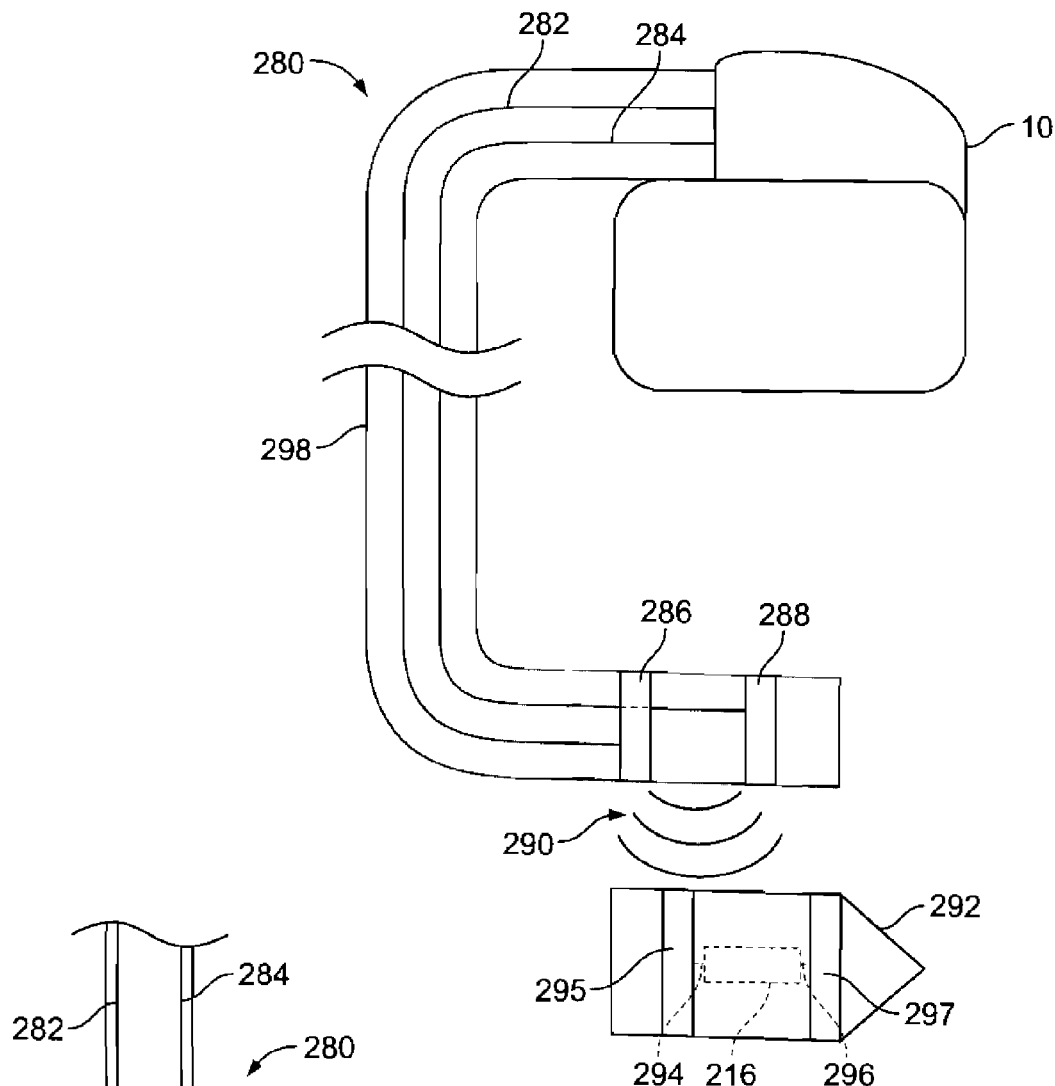
Figure 7B:
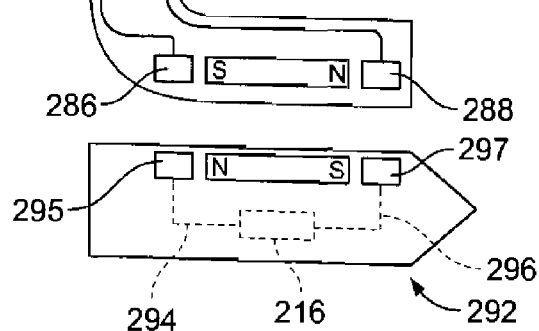
Figure 8:
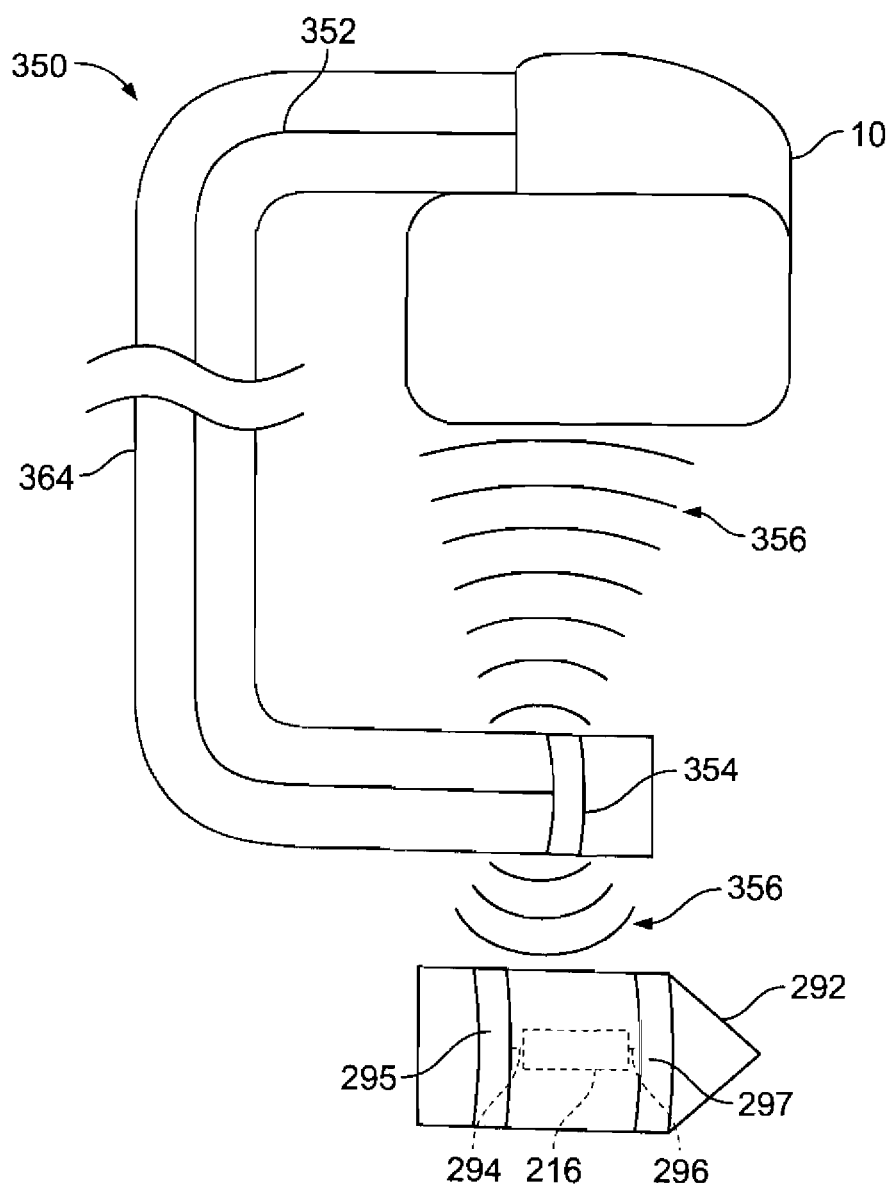

FIGS. 7-8 are diagrams of exemplary implementations that utilize electric field coupling between a leadless electrode assembly and a leaded device. In these implementations, alternating current may be passed through the heart tissues from the lead to the seed. Since the heart may not respond to frequencies above about 100 kHz, and since radiation and absorption by the conductive tissues of the heart may not be a limiting factor at frequencies below about a few megahertz, electric field frequencies in the 100 kHz to 2 MHz range may be used in various implementations.

Referring first to FIG. 7A, a diagram of an implementation that utilizes electric field coupling between a leadless electrode assembly and a leaded device is shown. For simplicity, a single bipolar lead 280 is shown attached to the pacing controller 10 in FIG. 7A. Lead 280 may correspond to lead 14 of FIG. 1 or lead 50 of FIG. 2, and the distal end of lead 280 may be positioned, for example, in the right ventricle, the coronary sinus, outside of the left ventricle near the apex of the heart, or at some other appropriate location in or near the heart. As is conventional, lead 280 includes a protective and insulating shroud 298, or lead body, which may be flexible and elongate, according to an implementation. Lead 280 may include a defibrillation coil for emergency defibrillation of the heart and may also employ separate electrodes (or electrodes 286 and/or 288, described below) to sense electrical signals from the adjacent heart tissue and to pace adjacent heart tissue.

In this simplified example, lead 280 contains electrically isolated first and second conductors or wires 282, 284, which are each connected to the pacing controller 10. The first wire 282 is also connected to a first electrode 286, and the second wire 284 is connected to a second electrode 288. The electrodes 286 and 288 are positioned on the exterior surface of lead 280 near the distal end of lead 280, and may facilitate electric field coupling with the leadless electrode assembly. Electrodes 286, 288 may be, for example, conventional ring electrodes, and may be separated on lead 280 by approximately 10 mm, according to an implementation. One of electrodes 286, 288 may alternatively be a tip electrode.

Electrodes 286 and 288 are not electrically connected, but may be appropriately positioned such that when time-varying current is passed from the pacing controller 10 through the first wire 282 to the first electrode 286, the current is able to flow across the space between the electrodes to the second electrode 288, and back to the pacing controller 10 through the second wire 284. This current flow generates an electric field 290. Examples of time-varying current may include alternating current or pulsed direct current.

Similarly, a wireless electrode assembly (seed) 292 contains a first wire 294 connected to a first seed electrode 295, and a second wire 296 connected to a second seed electrode 297, where the first and second seed electrodes 295, 297 are shown encircling the seed 292 on an exterior surface of the seed 292 in FIG. 7A. Wires 294 and 296 also are connected to a seed circuit 216 within the seed 292, which may include capability for charge storage, electrical stimulation (pace) delivery, electrical sense, and information transmit, receive and storage. Seed 292 may correspond to any of the seeds shown in FIGS. 1-4 and described above. In an implementation, the lead electrodes 286, 288 are separated by a distance greater than the distance separating the seed electrodes 295, 297. Electrodes 295 and 297 may receive energy from transmitter electrodes 286 and 288 for a majority of the cardiac cycle, in some implementations. Pacing energy may be delivered to the tissue through the same seed electrodes 295 and 297 at appropriate timing. Since a typical duration of a pacing pulse may be less than $\frac{1}{1,000}$th of the duration of time between pacing pulses, electrodes 295 and 297 may be connected in a "receive" mode for a vast majority of the cardiac cycle.

FIG. 7B shows another implementation using pad electrodes and magnets. As shown in FIG. 7B, the lead electrodes 286, 288 may be placed only on a side of the lead that faces the seed 292, and the seed electrodes 295 and 297 may be placed only on the side of the seed that faces the lead 280. In this case, the electrodes may be pad electrodes, or ring electrodes that are insulated except at portions of the ring that face the heart wall. An advantage of having electrodes only on the tissue side is that current flow may be confined to the tissues between the electrodes, and may not also flow through the electrically resistive blood pool. Energy transfer in this implementation may be orientation-dependent. To facilitate proper orientation between lead and seed, one or more magnets may be used with lead 280 proximate the lead electrodes 286 and 288, and one or more magnets may be used on seed 292 proximate the seed electrodes 295, 297. Using the attraction properties of the magnets, an orientation of the lead and seed can be configured so that the pad electrodes face one-another, as shown in the exemplary implementation of FIG. 7B.

Turning now to FIG. 8, a diagram of an implementation that utilizes electric field coupling at higher frequencies, such as above about 100 MHz, between a leadless electrode assembly and a leaded device is shown. For simplicity, a single unipolar lead 350 is shown attached to the pacing controller 10 in FIG. 8. Lead 350 may correspond to lead 14 of FIG. 1 or lead 50 of FIG. 2, and the distal end of the lead 350 may be positioned, for example, in the right ventricle, the coronary sinus, outside of the left ventricle near the apex of the heart, or at some other appropriate location in or near the heart. As is conventional, lead 350 includes a protective and insulating shroud 364, or lead body, which may be flexible and elongate, according to an implementation. In this simplified example, the lead 350 contains a single wire 352, which is connected to the pacing controller 10 and to a single lead electrode 354 positioned on an exterior surface of lead 350 and near the distal end of lead 350.

Electrode 354 is shown in FIG. 8 as a conventional ring electrode, but may alternatively be a tip electrode or a coil. In some implementations, electrode 354 may be only on the side of the lead that faces the seed (e.g., a pad electrode or ring electrode insulated except for a portion of the ring that faces the seed), as may be facilitated by providing orienting permanent magnets to the lead and seed. When time-varying current, such as alternating current or pulsed direct current is passed from the pacing controller 10 through the wire 352 to the lead electrode 354, current is able to flow back to the pacing controller 10, and an electric field 356 may be generated. The wireless electrode assembly (seed) 292 shown in FIG. 8 is identical to that shown in FIG. 7, and may be coupled by the electric field 356, permitting the transfer of charge energy and/or information from the leaded device to the seed 292. According to some implementations, efficient transfer of energy between lead electrode 354 and seed electrodes 295 and 297 may occur when the distance between the lead and seed conductors is an integral number of half-wavelengths of the transmitted energy. Since the exact distance between lead and seed may not be known until the seed and lead have been implanted, provisions may be made to sweep the frequency of the RF transmitter until resonant energy transfer is detected.

In each of the implementations described with respect to FIGS. 5-8, the lead or catheter may be described as containing a transmitting antenna, over which data and charge energy may be transmitted. Similarly, the seed may be described as containing a receiving antenna, by which corresponding data and/or charge energy may be received. In some implementations, seeds are capable of transmitting data and catheters/leads are capable of receiving data. It will be understood that the wires shown in FIGS. 5-8 are contained within the lead or within the seed, as appropriate, despite being shown in some cases with a solid line for simplicity, and similarly for the seed circuit 216 and transmitters and receivers. In some implementations, the magnets shown in FIGS. 5-8 may be within the lead or seed, while in other implementations the magnets may be on an exterior surface of the lead or seed. Magnets may optionally be used in any of the configurations described herein.

The seed circuit 216 has been described generally with respect to FIGS. 5-8. More specifically, the seed circuit 216 may contain a bridge rectifier connected across the receiver—that is, the coil 212 (FIG. 5), ultrasonic transducer 256 (FIGS. 6A, 6B), or electrodes 295, 297 (FIGS. 7A, 7B, 8)—to rectify the AC or pulsed DC current that is induced in the receiver by the magnetic field, ultrasonic beam, or electric field. In some implementations, a filter device may be connected across the receiver, and may pass only a single frequency of communication signal that is induced in the receiver. The single frequency of the communication signal that is passed by the filter device may be unique for the particular seed as compared to other implanted seeds. In this regard, the filter may be a narrow band pass filter with a frequency unique to a particular seed, and the incoming signal may be modulated with programming information. Alternatively, the filter may consist of any type of demodulator or decoder that receives analog or digital information induced by the leaded device in the receiver, including multimode communications. The received information may contain a code unique to each seed to command discharge of stored energy, along with more elaborate instructions controlling discharge parameters such as threshold voltage for firing, duration and shape of the discharge pulse, etc.

Regarding seed placement, in an implementation, the seeds may be delivered to their respective sites in the cardiac veins, within the heart wall, or on the epicardial surface of the heart via a catheter. A distal portion or tip of the catheter may contain a single electrode or a pair of electrodes, each being connected to a signal recorder via leads extending to a proximal end of the catheter. As such, it is possible to obtain a unipolar or bipolar ECG at the catheter distal tip. The physician may select the implantation site based upon features of the ECG signal sensed using the catheter. The seed may then be injected through a needle extended from the catheter tip, or it may be pushed into the tissue and then released from the catheter. Many mechanisms may be used for seed release, including the release or addition of fluid pressure to the catheter tip.

Once implanted, the seed may be charged and then fired to observe the altered electrogram proximate the seed at the location of the catheter tip. The physician may adjust the timing of seed firing by programming the pacing controller 10 using an external programming device. When satisfied with the electrograms, the catheter (or a seed delivery mechanism residing within the catheter) may be removed, and a new delivery mechanism containing the next pacing seed may be inserted and navigated to the next pacing site. Because seeds can be fired in any order, or not fired at all, a physician may deliver the seeds in any order. When the heart is deemed to be beating in synchrony, no further seeds need be implanted. Alternatively, if it has been determined that the seeds are small enough that they do not substantially impair local tissue function, then an array of seeds may be delivered to the veins and/or heart wall, and the physician can program a subset of seeds to fire in a sequence that optimizes the pumping efficiency of the heart. Ejection fraction and cardiac output, as well as blood pressure measured and communicated from one or more of the seeds in some implementations, may be measured to determine pumping efficiency. On any given heartbeat, some or all of the seeds may fire at the direction of the pacing controller 10, perhaps utilizing one or more (different) seeds to facilitate communication to the firing seed.

Figure 9A:
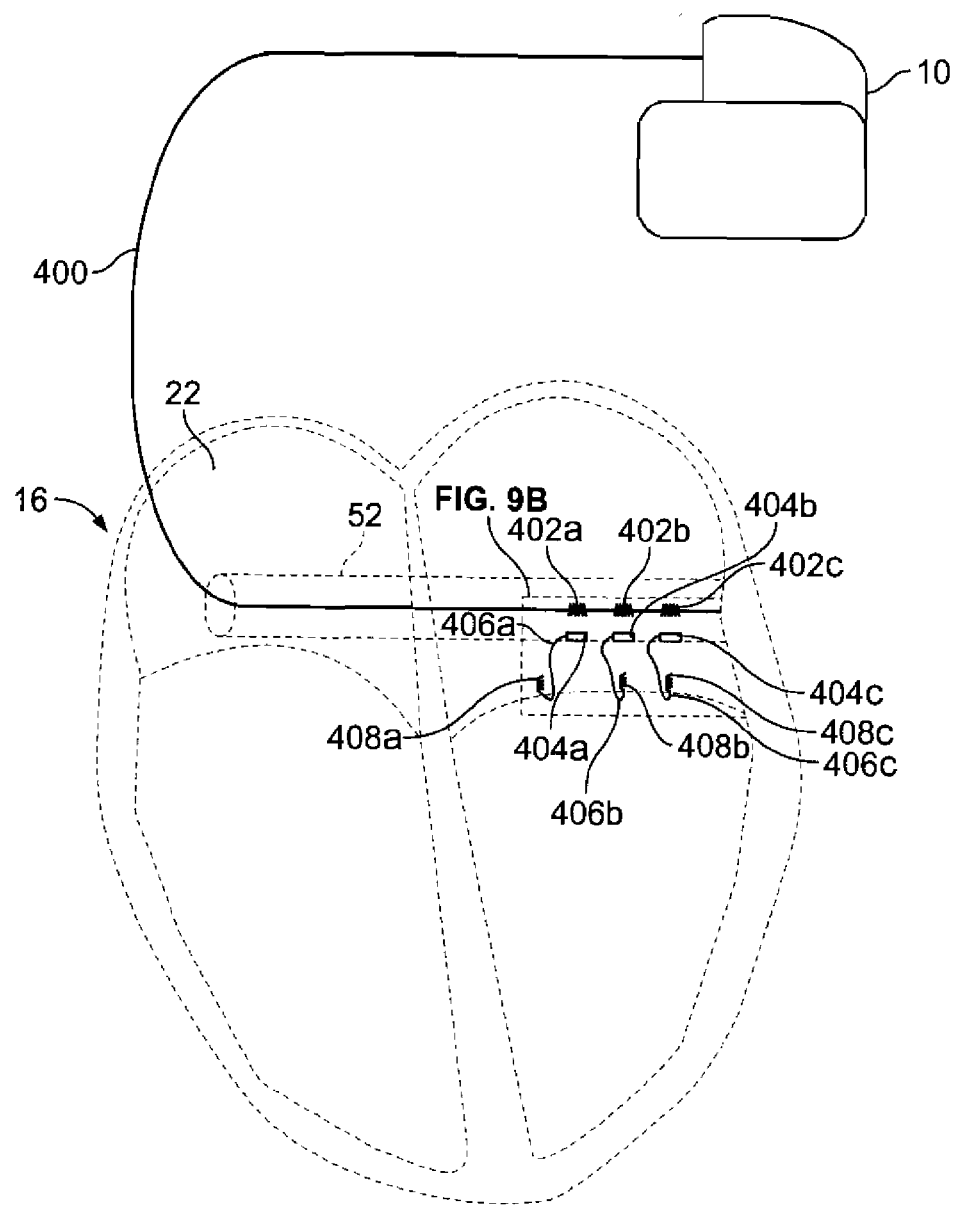
FIG. 9A is a diagram of an exemplary system that includes a leaded device having multiple transmitters on a single lead and multiple leadless electrode assemblies.
Figure 9B:
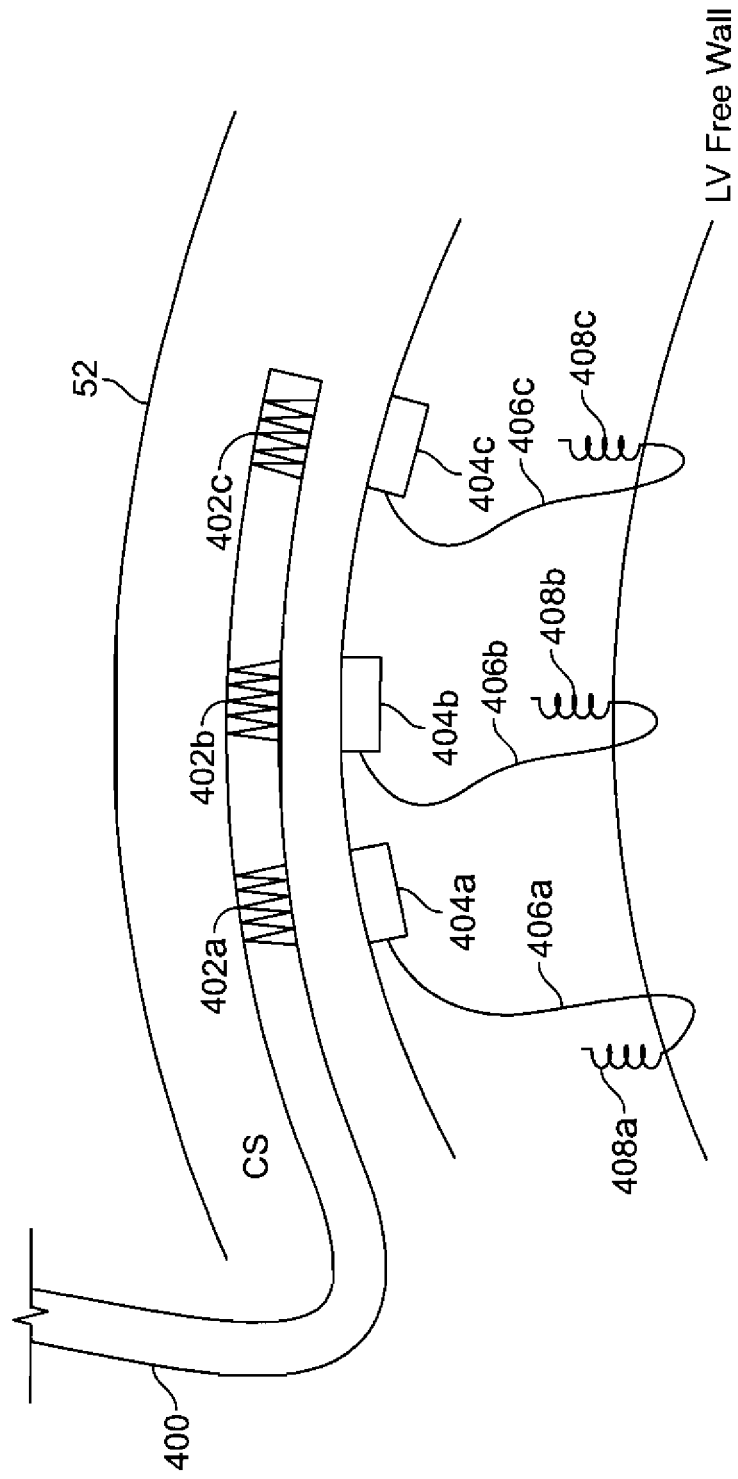
FIG. 9B is an expanded view of a portion of FIG. 9A.

In some implementations, a leaded device may utilize leads having multiple transmitters (or receivers, or transmitters/receivers (transceivers)). FIGS. 9A and 9B are diagrams of an exemplary system that includes a leaded device having multiple transmitters on a single lead and multiple leadless electrode assemblies. FIG. 9B is an expanded view of a portion of FIG. 9A. A lead 400 is connected to the pacing controller 10 at a proximate end, and passes through the right atrium 22 and into the coronary sinus 52. The lead contains three magnetic coils 402, each positioned near the distal end of the lead 400 within the coronary sinus 52 and near the left ventricle free wall. The coils 402 are connected to the pacing controller 10 through one or more lead conductors (not shown) that extend through the lead 400. The magnetic coils 402 transmit pacing energy, and may transmit information, to receiving leadless electrode assemblies 404. This energy and information originates from the pacing controller 10, and may be transmitted using techniques described above. In this example, the seeds 404 include magnets (not shown) to position the seeds in proximity to the magnetic coils 402, and to advantageously orient the seeds 404 for efficient reception of transmitted energy and/or data. The magnets may be housed within the seed in an implementation, or may be on an exterior surface of the seed 404 in other implementations. A magnetic force between the respective coils 402 and seeds 404 may hold the seeds 404 in the desired location, to permit efficient and tight coupling between transmitter and receiver. Micro lead wires 406 connect the seeds 404 to coil anchors 408, which are anchored to the left ventricle free wall. The seeds 404 may transmit pacing stimuli over the microleads 406 such that electrical stimuli may be imparted to tissue surrounding the coil anchors 408. In this implementation, the coil anchors 408 may serve as pace electrodes to surrounding tissue. As shown in FIG. 9, this configuration permits tight coupling between transmitter and receiver because of the close proximity with which transmitter and receiver are positioned, which may minimize losses, and yet permits pacing stimuli to be delivered to cardiac tissues at locations distant from either the locations of transmitter or receiver (namely, at the locations of the coil anchors 408).

Different implementations are possible, such as a series connection between the coils 402 and the controller 10 or independent connections between the controller 10 and each coil. In a series connection, a lead conductor may provide a single current path from the controller, through the coils 402a, 402b, and 402c, and back to the controller. If independent connections are used, isolated conductors may each supply independent current paths through the coils (perhaps including a common ground). A series connection may permit each coil 402 to transmit simultaneously, permitting each seed 404 to be recharged and/or receive data simultaneously. Conversely, independent connections between the controller 10 and the coils 402 through electrically isolated wires may permit the controller to implement diverse charge and command strategies, including not employing certain transmitter/receiver pairs. The seed assemblies 404 may correspond to any of the leadless electrode assemblies described herein, and in some implementations the coil anchors 408 and wires 406 may be omitted. In some implementations, multiple-transmitter leads may not include magnetic coils, but may instead include any of the transmitter types discussed above. In similar fashion, the seeds 404 need not include magnets.

Figures 10A, 10B:
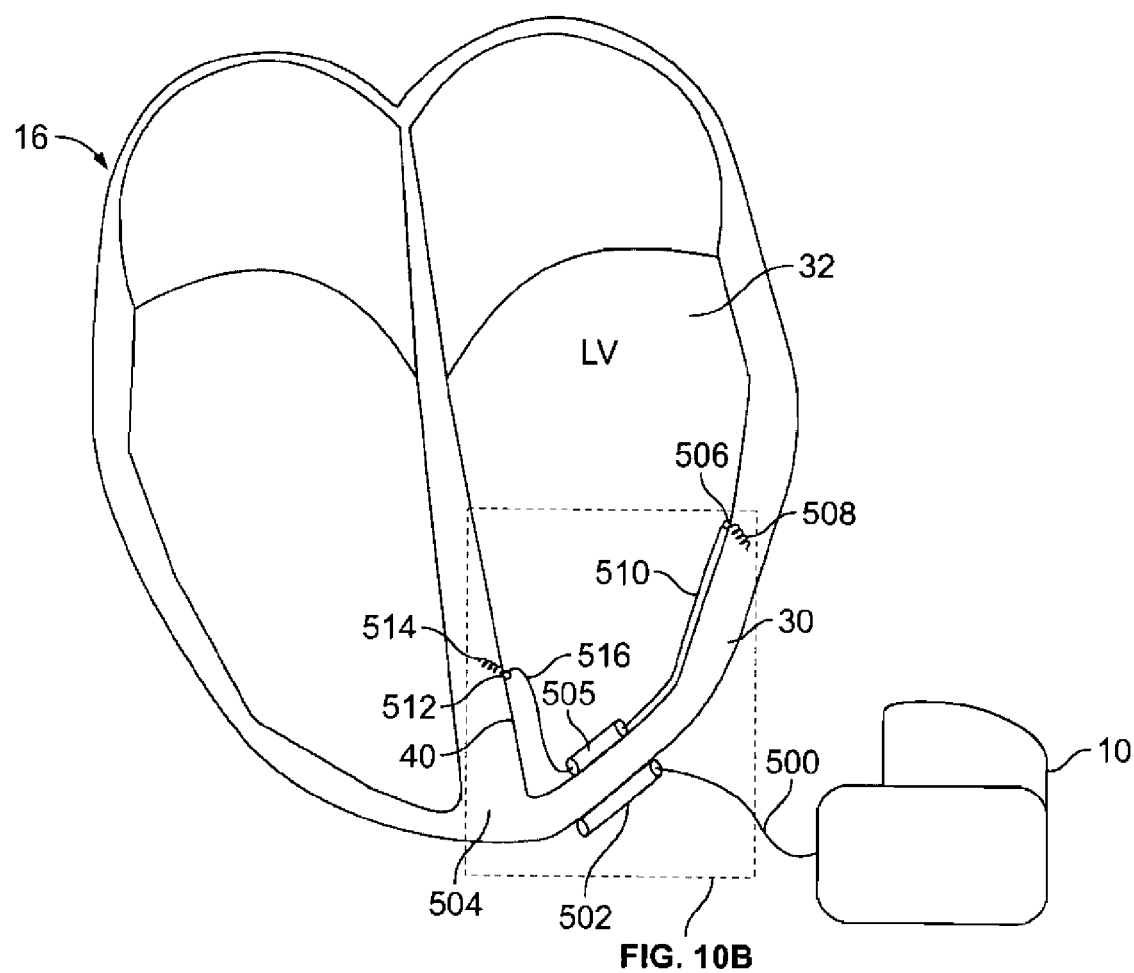
FIG. 10A is a diagram of a heart and another exemplary cardiac stimulation system using a leadless electrode assembly implanted in or near the heart.
FIG. 10B is an expanded view of a portion of FIG. 10A.
Figure 10B:
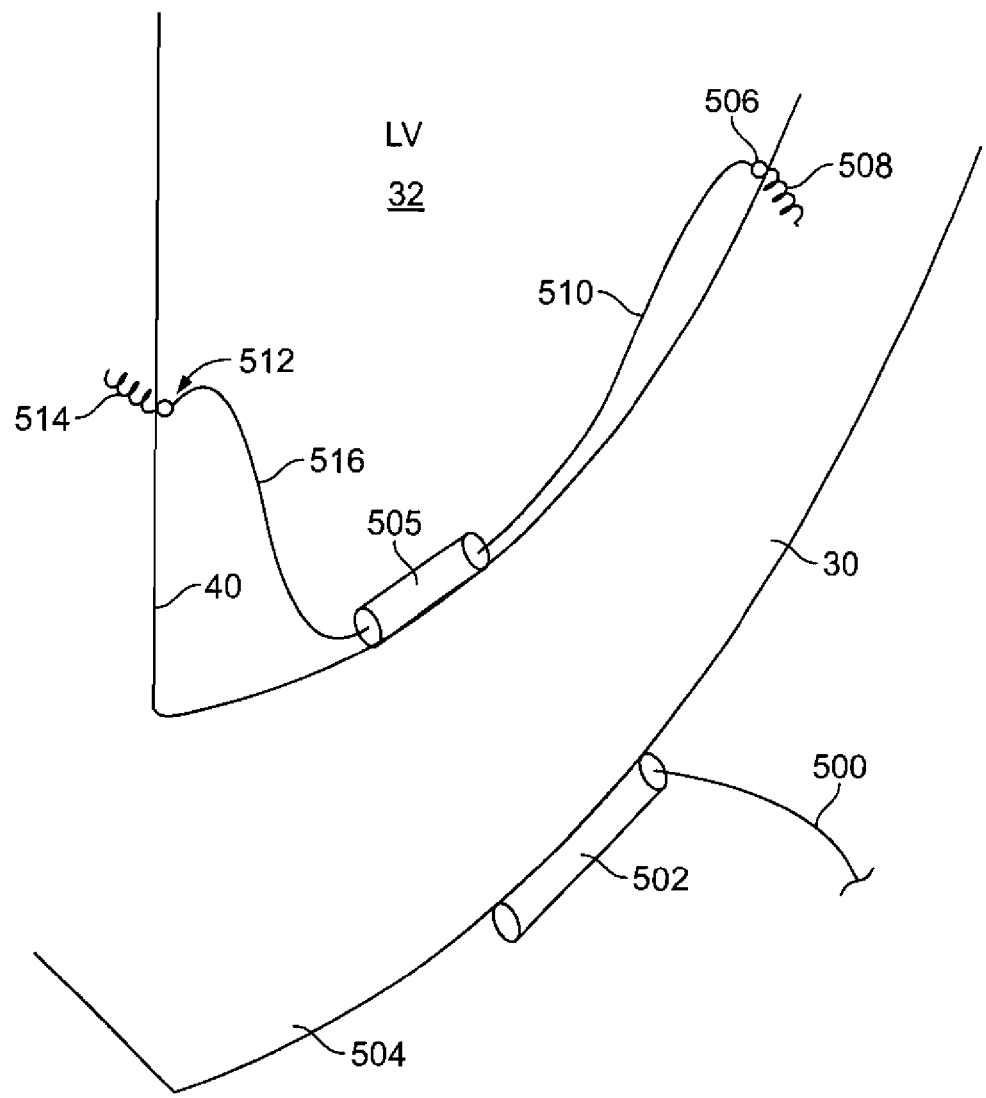

FIGS. 10A and 10B are diagrams of a heart 16 and another exemplary cardiac stimulation system using a leadless electrode assembly implanted in or near the heart. Referring first to FIG. 10A, a pacing controller 10 is shown having a lead 500 electrically connected to the pacing controller at a proximal end and extending from the pacing controller 10. A transmitter 502 is included near the distal end of the lead 500, and is positioned near an apex 504 of the heart 16. As described above with respect to the system shown in FIG. 1, the transmitter 502 may transmit energy or information via RF transmissions to leadless electrode assemblies, such as seed electrode assembly 505. Seed 505 may correspond to any of the seeds described previously in this document, and may be inductively coupled to receive transmitted charge energy or communications from the transmitter 502. The seed 505 may contain a charge storage device and a triggering mechanism to deliver stored electrical charge to adjacent heart tissue, according to an implementation.

In this implementation, the seed 505 is affixed to the inside of the left ventricle wall 30. FIG. 10A shows additional electrode assemblies 506, 512, which are electrically connected to the seed electrode assembly 505 via micro leads 510 and 516, respectively. As shown in FIG. 10A, electrode assembly 506 is affixed to the left ventricle free wall 30 via a helical tine fixation element 508, and electrode assembly 512 is affixed to the septal wall 40 of the left ventricle 32 via a helical tine fixation element 514. The seed electrode assembly 505 may pass energy or communications data, such as energy or communications received from the pacing controller 10 through the transmitter 502, to the additional electrode assemblies 506 and 512 over micro leads 510 and 516, respectively, and the electrode assemblies 506, 512 may then provide pacing stimulation to surrounding cardiac tissue. For example, electrode assembly 506 may provide pacing stimulation to surrounding tissue on the left ventricle free wall 30, and electrode assembly 512 may provide pacing stimulation to surrounding tissue on the septal wall 40 of the left ventricle 32. In this manner, cardiac synchronization may be improved as additional pacing sites may be realized in a coordinated fashion. More or fewer additional electrode assemblies 506, 512 may be included in other implementations. While the additional electrode assemblies 506, 512 are shown connected to the seed electrode assembly 505 via micro leads 510, 516, in other implementations the additional electrode assemblies 506, 512 may wirelessly communicate with the seed electrode assembly 505 or with the pacing controller 10 (through transmitter 502, for example). In these implementations, micro leads 510 and 516 may be omitted. FIG. 10B is an expanded view of a portion of FIG. 10A.

Figure 11:
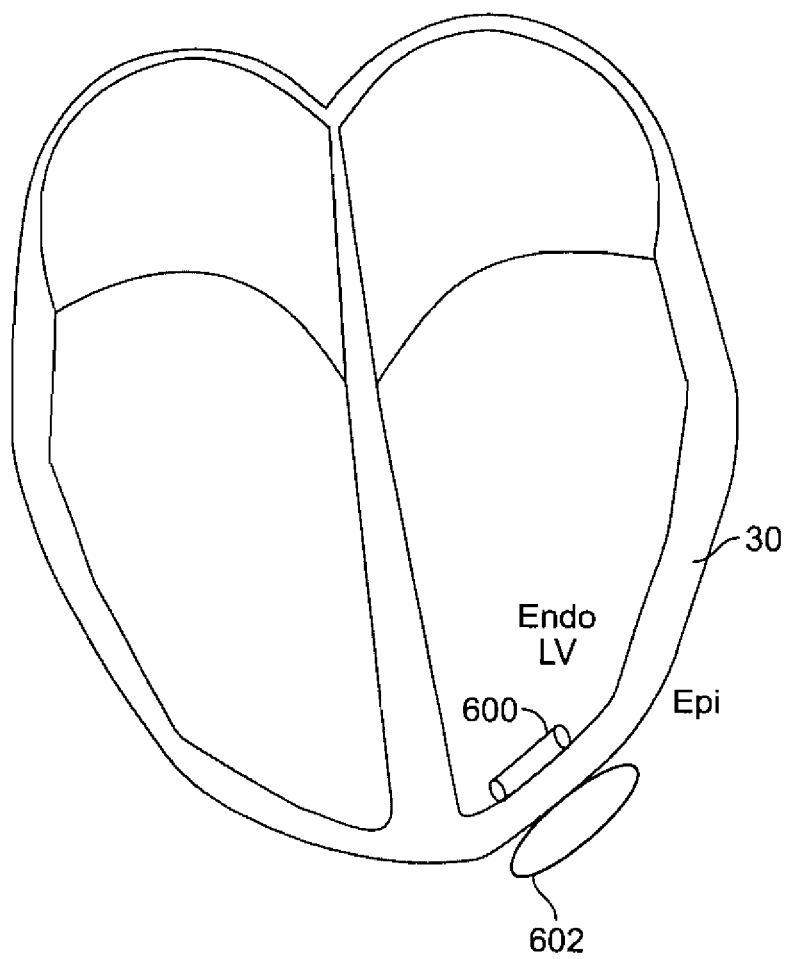
FIG. 11 is a diagram of a leadless electrode assembly in a heart chamber and a permanent magnet positioned on an epicardial surface of the heart.

Turning now to FIG. 11, permanent magnets may be advantageously utilized to position and orient leadless electrode assemblies at desirable pacing sites. In some implementations, magnets may be used to position and orient leadless electrode assemblies with respect to leaded transmitters such that more efficient field coupling may be realized. FIG. 11 is a diagram of a leadless electrode assembly 600 in a heart chamber and a permanent magnet 602 positioned on an epicardial surface of the heart. The seed 600 is held against an endocardial surface of the heart—here, against the free wall 30 of the left ventricle—by a magnetic force associated with the permanent magnet 602, which is affixed epicardially outside of the left ventricle in FIG. 11. The seed 600 may include a permanent magnet that is attracted by magnetic force to the magnet 602. Over time, fibrotic tissue growth may encroach upon the seed 600 and more permanently affix the seed to the corresponding cardiac surface. This may prevent unintended dislodgement of the seed from the wall surface.

Leads may also contain permanent magnets to orient and position seeds. For example, in the system shown in FIGS. 9A and 9B, magnets associated with coils 402 may position and orient seeds 404 using associated magnetic forces. These can be used to help align the transmitter coils 402 with the receiver coils in the seeds 404, such that more efficient and tighter coupling is possible. Alternatively, permanent magnets may also be used to position and orient catheters. In an implementation, the magnets 602 may be included in magnet assemblies, and may be utilized to advantageously position and orient seeds 26 or catheters/leads such that efficient inductive coupling between transmitter and receiver may occur.

In any of the implementations described herein, the use of permanent magnets as described above is optional. In certain implementations that use magnetic fields for energy transmission, the use of permanent magnets in the proximity of the ferrite core of induction coils may saturate all or part of the core, and may thereby reduce coupling efficiency. In some cases, this effect may be minimized by careful positioning of the permanent magnets relative to the ferrite cores. In other cases, the coil can be wound on the permanent magnet and characterized as an air core coil since strong permanent magnets will not react to the small field generated by the coils. Implementations that use electric fields and ultrasound for energy transmission may be unaffected by the presence of permanent magnets.

Referring again to FIG. 1, attractive magnetic forces between the magnet 602 and the seed 600 or catheter/lead may cause the seed 600 or catheter/lead to be held in a desired position such that unintended movement of the seed 600 or catheter/lead does not occur. Each magnet assembly may includes a permanent magnet 602 for supplying magnetic force and a fixation element (not shown in FIG. 11), such as a helical tine fixation element, for securing the magnet assembly to heart tissue.

In another implementation, a rod magnet is placed within a catheter near the transmitter and a second rod magnet, having opposite magnetic orientation from the first (that is, one magnet is a North-South magnet, and is aligned to a second magnet, which may be a South-North oriented magnet), is placed within the seed body near the receiver. Rod magnets may be placed within the catheter and within the seed body to provide the magnetic attraction to hold the transmitter and receiver in close proximity, in an appropriate orientation with respect to each other, or both. In an implementation, the rod magnets may be aligned approximately parallel to one another, such that the transmitter and receiver are appropriately oriented for efficient inductive coupling. Using magnets of opposite type may advantageously allow the magnets to collectively cancel each other out, such that magnetic attraction or repulsion to/from external magnets in the environment may be minimized. This may also aid in assuring MRI safety. This implementation may be appropriate for systems using electric field coupling or ultrasonic coupling, such as the systems described above in connection with FIGS. 6-8. For example, the implementations shown in FIGS. 6A, 6B, and 7B may utilize these concepts.

In another implementation, four button magnets may be used, with two near the transmitter and two near the receiver. In this example, one button magnet may be placed near each end of the transmitter, and similarly one button magnet may be placed near each end of the receiver. Magnetization here may be perpendicular to the axis of the seed. This implementation may be appropriate for systems using magnetic field coupling, such as the system described above in connection with FIG. 5.

Figure 12:
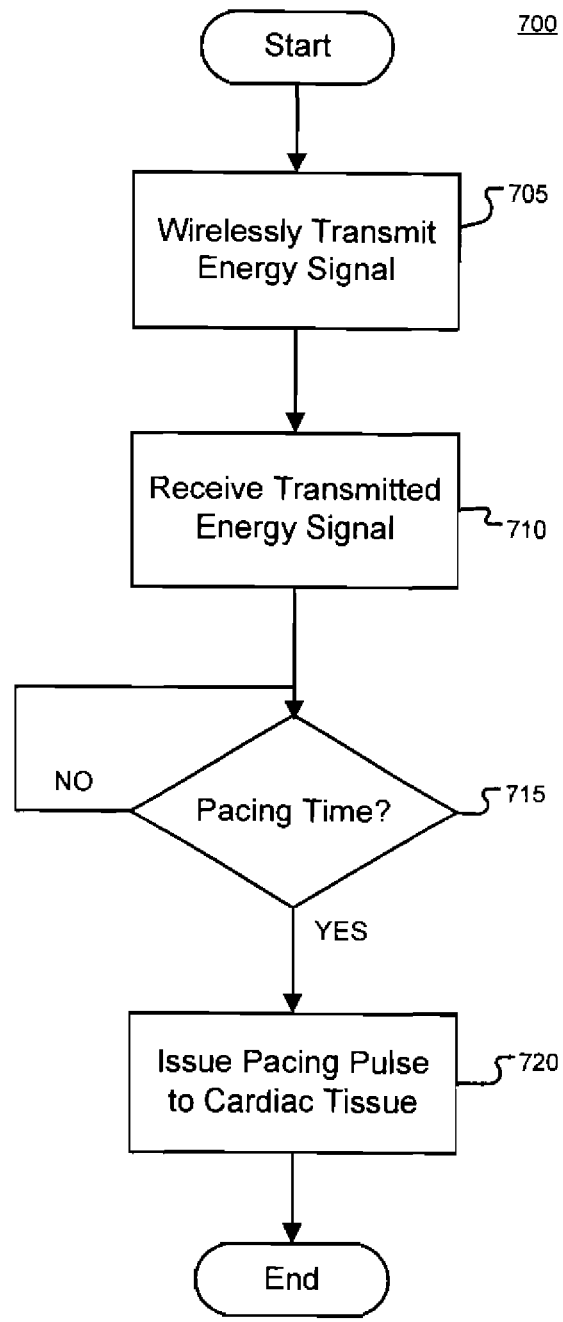
FIGS. 12-13 are flow charts of exemplary operations that can be performed by the systems of FIGS. 1-3 and 5-10.
Figure 13:
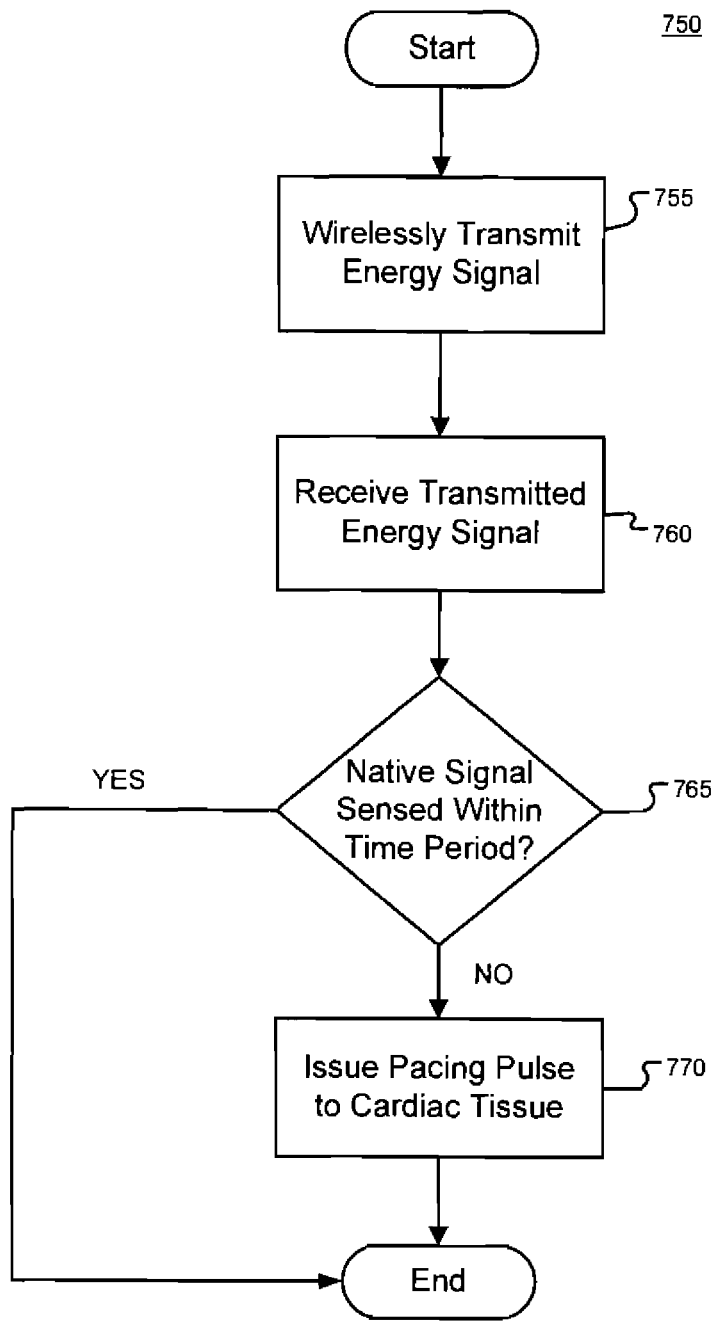

FIGS. 12-13 are flow charts of exemplary operations that can be performed by the systems of FIGS. 1-3 and 5-10. Referring first to FIG. 12, a method 700 of operating a cardiac pacing system begins, at step 705, with the wireless transmission of an energy signal. The energy signal may be transmitted by a transmitter that includes a wired lead whose distal end is positioned in a first chamber of a heart, according to an implementation. The energy transmission may include pacing energy, pacing information, or both, and may be effected by a generation of an electric field, a magnetic field, or an ultrasonic beam, according to some implementations. At step 710, the transmitted energy signal may be received. In an implementation, a wireless pacing electrode assembly positioned within a second chamber of the heart may receive the energy transmission. In some implementations, more than one wireless pacing electrode assembly may receive the transmitted energy signal, which may be transmitted from a single transmitter or multiple transmitters. In an implementation, the first chamber is a right ventricle of the heart and the second chamber is a left ventricle of the heart.

If it is time to deliver a pacing pulse at step 715, a pacing pulse may be issued to cardiac tissue at step 720. In an implementation, the wireless pacing electrode assembly may issue the pacing pulse to surrounding cardiac tissue in the second chamber of the heart. In some implementations, the wireless electrode assembly may determine the pacing time at step 715. In other implementations, a pacing controller may determine an appropriate pacing time, and may command the wireless electrode assembly to deliver the pacing pulse at the determined time. This might occur in several ways. For example, the controller may transmit pacing energy to the wireless assembly, which the assembly may store. Then, at the pacing time, the controller may transmit a pace trigger signal to the wireless assembly, which may cause the assembly to issue the pacing pulse to surrounding cardiac tissue. In another example, the wireless assembly and the pacing controller may be synchronized to a timing schedule, as by each including a time-keeping circuit, and the pacing controller may communicate pacing times to the wireless assembly. In some implementations, step 715 may be omitted and the wireless electrode assembly may issue the pacing pulse at step 720 after receipt of the transmitted signal.

Turning now to FIG. 13, another method 750 of operating a cardiac pacing system is shown. An energy signal is wirelessly transmitted at step 755, and the transmitted signal is received at step 760. These two steps 755, 760 may be identical to steps 705 and 710, respectively, described above with reference to FIG. 12, according to some implementations. At step 765, sense circuitry monitors for detection of a native cardiac electrical signal within a specified time period from the receipt of the transmitted signal. In an implementation, the wireless electrode assembly includes sense circuitry to sense the native cardiac electrical signal and timing circuitry to implement a monitoring period.

If the patient is in normal sinus rhythm, the native cardiac electrical signal originates at the sino-atrial node of the heart, and may be sensed by controller 10 via right atrial lead 12. The controller may be programmed to deliver pacing pulses to leads in the ventricles at specific time delays relative to the sensed sinus beat (usually somewhat more than 100 msec, and may be a function of exertion sensed by an embedded accelerometer). Ventricle leads may be instructed to pace simultaneously or sequentially in a pattern that has been found to optimize cardiac hemodynamics. If the patient is being paced in the right atrium, the delays can be computed relative to the right atrium pacing pulse. If a native cardiac electrical signal is sensed at a given ventricle seed electrode before the programmed delay period has expired in step 765, the method ends. If, however, a native cardiac electrical signal is not sensed within the specified time period at step 765, a pacing pulse is issued to cardiac tissue at step 770. In an implementation, the wireless electrode assembly may issue or withhold the pacing pulse. In another implementation, the local signal sensed at the pacing site may be communicated to the controller 10, and if a native pacing signal is sensed within the delay period, the controller may not transmit pacing energy to the seed.

Figure 14:
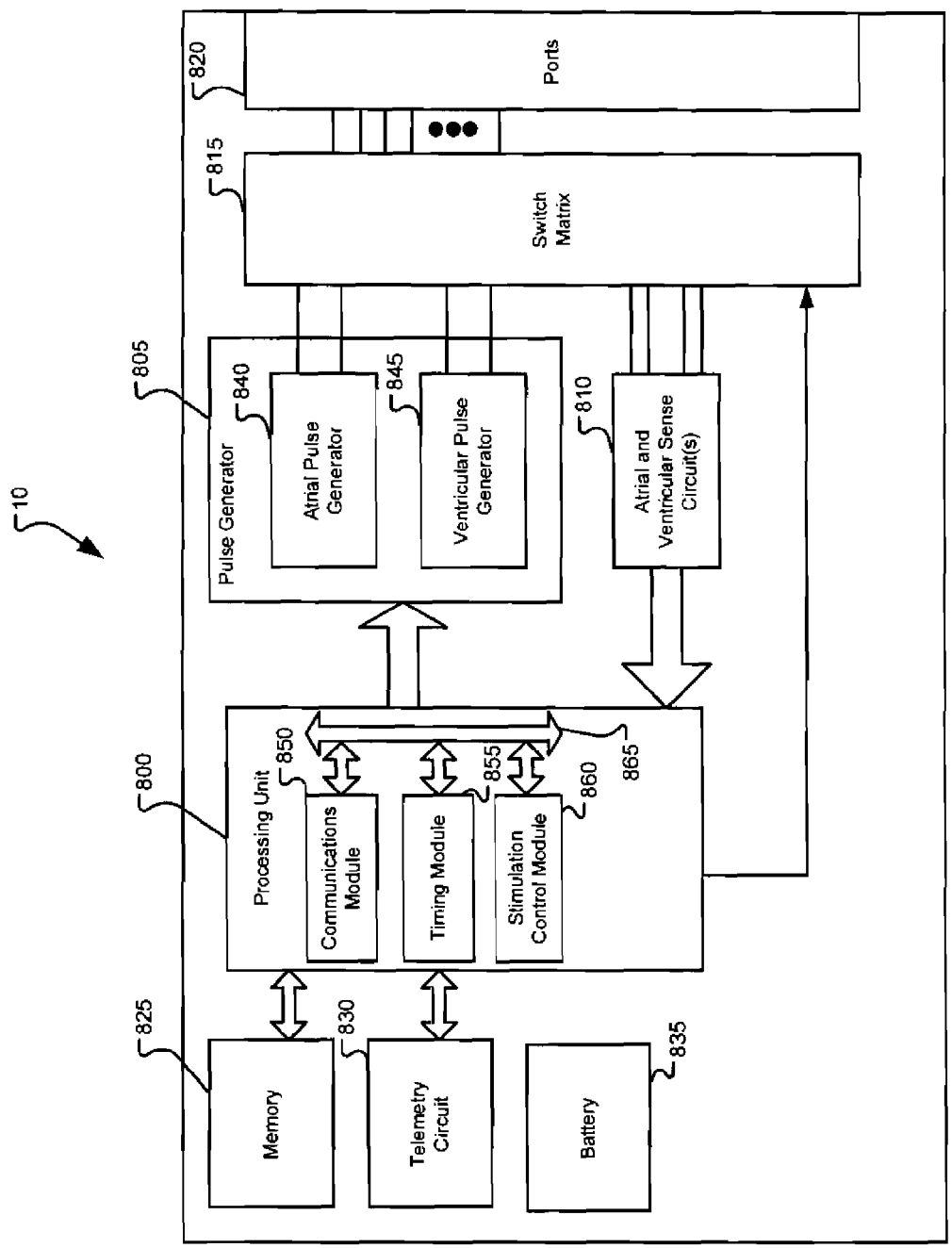
FIG. 14 is an exemplary block diagram of a pacing controller that may be used with the systems of FIGS. 1-3 and 5-10.

FIG. 14 is an exemplary block diagram of a pacing controller 10 that may be used with the systems of FIGS. 1-3 and 5-10. The exemplary pacing controller 10 includes circuits for communicating wirelessly with a wireless electrode assembly using a transmitter on an attached lead whose distal end is implanted in a chamber of the heart, or outside a chamber of the heart. In an implementation, the pacing controller 10 includes a processing unit 800, a pulse generator 805, one or more sense circuits 810, a switch matrix 815, a series of ports 820 into which leads may attach, memory 825, a telemetry circuit 830, and a battery 835. The processing unit 800 may be a programmable micro-controller or microprocessor, and may include one or more programmable logic devices (PLDs) or application specific integrated circuits (ASICs). The processing unit 800 may execute instructions and perform desired tasks as specified by the instructions. The memory 825 may include volatile and non-volatile memory, and may store the instructions that when executed by the processing unit 800 cause methods and processes to be performed by the pacing controller 10. In some implementations, the processing unit 800 may include memory as well. The memory 825 may be used to store pacing parameters and sensed information according to some implementations. The telemetry circuit 830 permits wireless RF communication with an external computing device, such as a programming device, such that information may be provided to the pacing controller 10 or supplied to the external computing device. The battery 835 supplies power to the circuits and modules of the pacing controller 10.

The pulse generator 805 may include one or more atrial pulse generator circuits 840 and one or more ventricular pulse generator circuits 845, each of which may generate pulses for transmission through the switch matrix 815 to a desired port, into which a cardiac lead may attach. Each pulse generator may include a current generation circuit, which may be capable of generating current, including time-varying current such as alternating current or pulsed direct current. The pulse generators may operate under the guidance of the processing unit 800, according to an implementation. In an implementation, the processing unit 800 directs the pulse generator 805 to generate an appropriate time-varying current that when passed through a lead conductor to a transmitter implanted in a first chamber of the heart, an electric, magnetic, or ultrasonic field is generated to couple a receiver in a wireless electrode assembly positioned in a second chamber of the heart for the transmission and reception of pacing energy, pacing information, or both.

The processing unit 800 includes a communications module 850, a timing module 855, and a stimulation control module 860, each connected by a communications bus 865. The processing unit may additionally include digital-to-analog (D/A) converters, analog-to-digital (A/D) converters, timers, counters, filters, switches, etc. (not shown). The communications module 850, timing control module 855, and stimulation control module 860 may work individually or in concert to provide pacing stimuli to the heart and to control communication between a leaded transmitter and one or more leadless electrode assemblies. In an implementation, the processing unit 800 may encode information, such as a unique identifier, pacing threshold information, pulse width information, pacing trigger signals, demand pacing information, pace timing information, and the like, to be transmitted to the wireless electrode assemblies. The processing unit 800 may supply appropriate control signals to the pulse generator 805 to cause the pulse generator 805 to appropriately supply current to a leaded transmitter through the switch matrix 815, a corresponding port, and a lead conductor through an attached lead to cause the transmitter to emit an electric field, magnetic field, or ultrasonic beam, depending on type of transmitter utilized in the implementation. A receiver on the leadless electrode assembly may receive this information, decode and store it, and may use the information to issue pacing stimuli to surrounding cardiac tissue. The processing unit 800 may similarly control the pulse generator 805 to transmit pacing energy to the wireless electrode assembly, which may be stored and used to issue the pacing stimuli in a chamber of the heart different from the chamber in which the transmitter resides. Pacing energy may be delivered to the tissue directly upon receipt, or it may be stored until a low level communication trigger signal is received from the controller via the lead transducer.

Information from the sense circuits 810 may be used to adjust pacing or communications parameters. The sense circuits may amplify and filter signals sensed from sensors positioned in the right or left atrium, or in the right or left ventricle, or from sensors on an external surface of the pacing controller. As is conventional, the sense circuits 810 may include one or more A/D converters. The sensors may be attached to leads implanted within the heart, and in some implementations the wireless electrode assemblies may include sensors and may transmit sensed information to the pacing controller 10 directly or through a lead that includes a receiver. In some implementations, the seed electrodes that deliver pacing energy to the tissue are the same as the sense electrodes used to sense the local electrical voltage at the pacing site. In these cases, sensing may be blanked when pacing energy is being delivered. Similarly, the transducer that receives pacing energy and communications may be the same as the transducer that sends sensed information back to the controller, according to some implementations. In these cases, outgoing transmissions may be blanked when energy or communication is being received. The pacing controller 10 may include one or more can or housing electrodes on an exterior surface of the controller.

The switch matrix 815 includes a collection of switches, and may permit the pulse generators 840, 845 or the sense circuits 810 to be electrically connected to any of the available ports 820. The switch matrix 815 may be controlled by the processing unit 800, according to an implementation. The ports 820, as is conventional, provide attachment points where proximal lead ends may be attached to provide electrical connections between the pacing controller 10 and attached leads. One or more right atrial, right ventricle, coronary sinus, left atrial, or left ventricle ports may be provided, as well as electrical connection to the one or more can electrodes.

A number of implementations have been described. Nevertheless, it will be understood that various modifications may be made without departing from the spirit and scope of the systems, devices and techniques described in this document. Accordingly, other embodiments are within the scope of the following claims.

What is claimed is:

1. A cardiac tissue excitation lead, comprising:
   a flexible elongate lead body having a proximal end adapted to be inserted into an implantable pulse generator assembly and having a distal end adapted to be positioned within a heart;
   one or more lead conductors extending within the lead body; and
   a plurality of transmitter assemblies located at different locations along a length of the lead body near the distal end of the lead body and electrically connected to the pulse generator assembly via the one or more lead conductors to wirelessly transmit pacing control information and pacing energy from respective transmitter assemblies to respective implantable leadless electrode assemblies;

wherein the respective transmitter assemblies include at least one transmitter assembly that is configured to control a respective implantable leadless electrode assembly independently of other leadless electrode assemblies.

2. The cardiac tissue excitation lead of claim 1, wherein at least one of the plurality of transmitter assemblies comprises a coil wound around a ferrite core.

3. The cardiac tissue excitation lead of claim 2, wherein the wireless transmission of pacing control information and pacing energy occurs when the pulse generator assembly supplies a time-varying current to the coil through the lead conductor to emit a magnetic field.

4. The cardiac tissue excitation lead of claim 1, wherein at least one of the plurality of transmitter assemblies comprises an ultrasonic transducer.

5. The cardiac tissue excitation lead of claim 4, wherein the wireless transmission of pacing control information and pacing energy occurs when the pulse generator assembly supplies an electrical current to the ultrasonic transducer through the lead conductor to emit an ultrasonic beam.

6. The cardiac tissue excitation lead of claim 1, wherein at least one of the plurality of transmitter assemblies comprises a pair of separated electrodes.

7. The cardiac tissue excitation lead of claim 6, wherein the wireless transmission of pacing control information and pacing energy occurs when the pulse generator assembly supplies a time-varying current through the lead conductor across the pair of separated electrodes to emit an electric field.

8. The cardiac tissue excitation lead of claim 1, further comprising a first magnet positioned near at least one of the plurality of transmitter assemblies that magnetically attracts a second magnet included with a respective leadless electrode assembly to orient the transmitter assembly and the respective leadless electrode assembly.

9. The cardiac tissue excitation lead of claim 1, wherein the pacing control information includes pace timing information and a pace trigger signal.

10. The cardiac tissue excitation lead of claim 1, wherein each of the transmitter assemblies in the plurality of transmitter assemblies transmits pacing control information and pacing energy to a different implantable leadless electrode assembly in a plurality of respective implantable leadless electrode assemblies.

11. The cardiac tissue excitation lead of claim 1, wherein the respective transmitter assemblies are configured to be coupled to the implantable pulse generator assembly including coupling to a pacing controller unit that is commonly shared amongst the respective transmitter assemblies.

12. An implantable cardiac tissue excitation system, comprising:

an implantable pacing controller unit comprising a pulse generation circuit;

a lead comprising a lead body extending between a proximal lead end attachable to the pacing controller unit and a distal lead end configured to be implanted within a heart, one or more lead conductors extending within the lead body, and a plurality of transmitter assemblies located at different locations along a length of the lead body near the distal lead end, the transmitter assemblies electrically connected to the pulse generation circuit through at least one lead conductor to wirelessly transmit pacing control information and charge energy from the transmitter assemblies when the pulse generation circuit provides an electrical current to the transmitter assemblies through the lead conductor; and respective leadless electrode assemblies configured to be implanted within the heart and each comprising a receiver to receive the wireless transmission from a respective lead transmitter assembly, a charge storage unit to store the charge energy, and an electrical stimulation circuit to deliver an electrical stimulus to cardiac tissue using the pacing control information and the charge energy;

wherein the respective transmitter assemblies include at least one transmitter assembly that is configured to control a respective implanted leadless electrode assembly independently of the other leadless electrode assemblies according to control signals from the implantable pacing controller unit.

13. The implantable cardiac tissue excitation system of claim 12, further comprising implantable remote pacing stimulators in communicable contact with a respective leadless electrode assembly, each of the one or more remote pacing stimulators located in the heart and configured to apply pacing stimuli to surrounding heart tissue at the direction of the respective leadless electrode assembly.

14. The implantable cardiac tissue excitation system of claim 13, wherein each of the remote pacing stimulators communicates with the respective leadless electrode assembly wirelessly.

15. The implantable cardiac tissue excitation system of claim 13, wherein each of the one or more remote pacing stimulators communicates with the respective leadless electrode assembly over a wire between the respective leadless electrode assembly and the remote pacing stimulator.

16. The implantable cardiac tissue excitation system of claim 12, wherein a respective leadless electrode assembly further comprises a sense circuit for sensing electrical cardiac activity and a transmitter for wirelessly transmitting information associated with the sensed electrical cardiac activity.

17. The implantable cardiac tissue excitation system of claim 12, wherein the pacing controller passes a time-varying current through a respective transmitter assembly to generate an electric field to transmit the pacing control information and charge energy.

18. The implantable cardiac tissue excitation system of claim 12, wherein a respective transmitter assembly comprises a coil enclosing at least a portion of a ferrite core.

19. The implantable cardiac tissue excitation system of claim 18, wherein the pacing controller passes a time-varying current through the coil to generate a magnetic field to transmit the pacing control information and charge energy.

20. The implantable cardiac tissue excitation system of claim 12, wherein a respective transmitter assembly comprises a magnetic coil.

21. The implantable cardiac tissue excitation system of claim 20, wherein a respective leadless electrode assembly includes a magnet, and wherein a magnetic force between the magnetic coil and the magnet assists in orienting the respective leadless electrode assembly.

22. The implantable cardiac tissue excitation system of claim 12, further comprising a magnet assembly configured to be affixed to a heart wall and including a magnet that attracts a magnet included in a respective leadless assembly to position the respective leadless electrode assembly.

23. A method of operating a cardiac pacing system, the method comprising:

transmitting respective energy signals wirelessly using a wired lead whose distal end is positioned within a heart, using respective transmitter assemblies located at different locations along a length of a lead body of the wired lead near the distal end, and whose proximal end is coupled to a pulse generator;

receiving the transmitted energy signals at respective wireless pacing electrode assemblies coupled respectively to the respective transmitter assemblies, the respective transmitter assemblies positioned within the heart; and controlling issuance of a pacing pulse from a respective wireless pacing electrode independently of other wireless pacing electrodes using a respective transmitter assembly.

24. The method of claim 23, wherein the energy transmission comprises charging energy and pacing information.

25. The method of claim 23, wherein transmitting a respective energy signal wirelessly from the wired lead comprises generating an electric field created at the wired lead positioned in a first chamber of the heart.

26. The method of claim 23, wherein transmitting a respective energy signal wirelessly from a wired lead comprises generating a magnetic field created at the wired lead positioned in a first chamber of the heart.

27. The method of claim 23, wherein transmitting a respective energy signal wirelessly from a wired lead comprises generating an ultrasonic beam at the wired lead positioned in a first chamber of the heart.

28. The method of claim 23, wherein a plurality of wireless pacing electrode assemblies receive respective transmitted energy signals.

29. The method of claim 23, wherein the distal end of the wired lead is positioned in a first chamber of the heart and at least one of the wireless pacing electrode assemblies is positioned in a second, different chamber of the heart.

30. The method of claim 29, wherein the first chamber is a right ventricle of the heart and the second chamber is a left ventricle of the heart.

31. A method of operating a cardiac pacing system, the method comprising:

transmitting respective energy signals wirelessly using a wired lead whose distal end is positioned in a first chamber of a heart, using respective transmitter assemblies located at different locations along a length of a lead body of the wired lead near the distal end, and whose proximal end is coupled to a pulse generator;

receiving the transmitted energy signals at respective wireless pacing electrode assemblies coupled respectively to the respective transmitter assemblies, the respective transmitter assemblies positioned within a second chamber of the heart; and controlling issuance of a pacing pulse from a respective wireless pacing electrode assembly independently of other wireless pacing electrode assemblies using a respective transmitter assembly, including inhibiting issuance of a pacing pulse when a native cardiac electrical signal is sensed by the respective wireless pacing electrode assembly within a specified time period from receipt of a respective transmitted energy signal by the respective wireless pacing electrode assembly.

32. The method of claim 31, wherein the energy transmission comprises charging energy and pacing information.

33. The method of claim 31, wherein a respective wireless pacing electrode assembly includes sense circuitry to sense the native cardiac electrical signal.

34. The method of claim 31, wherein transmitting a respective energy signal wirelessly from the wired lead comprises generating an electric field created at the wired lead implanted in the first chamber of the heart.

35. The method of claim 31, wherein transmitting a respective energy signal wirelessly from the wired lead comprises generating a magnetic field created at the wired lead implanted in the first chamber of the heart.

36. The method of claim 31, wherein transmitting a respective energy signal wirelessly from the wired lead comprises generating an ultrasonic beam at the wired lead implanted in the first chamber of the heart.

37. The method of claim 31, wherein the native cardiac electrical signal originates at a sino-atrial node of the heart.

\* \* \* \* \*